(12) United States Patent
Zhang et al.

(10) Patent No.: US 11,708,616 B2
(45) Date of Patent: Jul. 25, 2023

(54) **METHODS FOR DETECTION OF ANTIBIOTIC RESISTANT *H. PYLORI***

(71) Applicant: AMERICAN MOLECULAR LABORATORIES INC., Vernon Hills, IL (US)

(72) Inventors: Hongjun Zhang, Vernon Hills, IL (US); Yi Zhou, Vernon Hills, IL (US); Rajarao Kakuturu, Vernon Hills, IL (US)

(73) Assignee: AMERICAN MOLECULAR LABORATORIES INC., Vernon Hills, IL (US)

( * ) Notice: Subject to any disclaimer, the term of this patent is extended or adjusted under 35 U.S.C. 154(b) by 238 days.

(21) Appl. No.: 16/764,765

(22) PCT Filed: Nov. 16, 2018

(86) PCT No.: PCT/US2018/061439
§ 371 (c)(1),
(2) Date: May 15, 2020

(87) PCT Pub. No.: WO2019/099775
PCT Pub. Date: May 23, 2019

(65) Prior Publication Data
US 2020/0399685 A1     Dec. 24, 2020

Related U.S. Application Data

(60) Provisional application No. 62/587,097, filed on Nov. 16, 2017.

(51) Int. Cl.
*C12Q 1/68* (2018.01)
*A61K 39/40* (2006.01)
*C12Q 1/689* (2018.01)

(52) U.S. Cl.
CPC .............. *C12Q 1/689* (2013.01); *A61K 39/40* (2013.01); *C12Q 2600/156* (2013.01)

(58) Field of Classification Search
CPC .......................... C12Q 2600/156; A61K 39/40
See application file for complete search history.

(56) References Cited

U.S. PATENT DOCUMENTS

| | | | | |
|---|---|---|---|---|
| 10,968,489 | B2 * | 4/2021 | Zhou | C12Q 1/6827 |
| 2016/0040215 | A1 * | 2/2016 | Henn | C12Q 1/689 |
| | | | | 435/6.12 |
| 2016/0201115 | A1 | 7/2016 | Colman et al. | |
| 2017/0327873 | A1 * | 11/2017 | Zhou | C12Q 1/689 |

FOREIGN PATENT DOCUMENTS

| | | | | |
|---|---|---|---|---|
| CN | 104846097 A | * | 8/2015 | .......... C12Q 1/6858 |

OTHER PUBLICATIONS

Chen, H. and Jiang, W., 2014. Application of high-throughput sequencing in understanding human oral microbiome related with health and disease. Frontiers in microbiology, 5: 508 pp. 1-6. (Year: 2014).*
Horemans et al., 2011. An alternative, sensitive method to detect Helicobacter pylori DNA in feces. Helicobacter, 16(2), pp. 113-118. (Year: 2011).*
Li et al. 2008. Improved RNA quality and TaqMan® Pre-amplification method (PreAmp) to enhance expression analysis from formalin fixed paraffin embedded (FFPE) materials. Bmc Biotechnology, 8(1), pp. 1-11. (Year: 2008).*
Sugimoto et al., 2009. Unreliability of results of PCR detection of Helicobacter pylori in clinical or environmental samples. Journal of clinical microbiology, 47(3), pp. 738-742. (Year: 2009).*
Zou et al., English Translation of CN-104846097A, pub. Aug. 19, 2015, priority May 21, 2015. (Year: 2015).*
Dietrich et al., 2013. Improved PCR performance using template DNA from formalin-fixed and paraffin-embedded tissues by overcoming PCR inhibition. PLoS One, 8(10), e77771 pp. 1-10. (Year: 2013).*
Mitsui et al., S., 2010. Multiplexed resequencing analysis to identify rare variants in pooled DNA with barcode indexing using next-generation sequencer. Journal of human genetics, 55(7), pp. 448-455. (Year: 2010).*
Colman et al. Rapid Drug Susceptibility Testing of Drug-Resistant *Mycobacterium tuberculosis* Isolates Directly from Clinical Samples by Use of Amplimn Sequencing: a Proof-of-Concept Study, Journal of clinical microbiology, Jul. 25, 2016 vol. 54, No. 8, pp. 2058-2067. Entire document.
Wang et al. Somatic Mutation Screening Using Archival Formalin-Fixed, Paraffin-Embedded Tissues by Fluidigm Multiplex PCR and Illumina Sequencing, The Journal of molecular diagnostics, Sep. 2015, vol. 17, No. 5, pp. 521-532. Entire document, especially p. 525.
Nishizawa et al. Mechanisms of Helicobacter pylori antibiotic resistance and molecular testing, Frontiers in molecular biosciences, Oct. 24, 2014, vol. 1, No. 19. Entire document, especially p. 4, col. 1.
International Search Report and Written Opinion for International Application No. PCT/US2018/06439.

* cited by examiner

*Primary Examiner* — Teresa E Strzelecka
*Assistant Examiner* — Olayinka A Oyeyemi
(74) *Attorney, Agent, or Firm* — Morgan, Lewis & Bockius LLP

(57) ABSTRACT

The present disclosure provides methods and materials for determining if antibiotic resistant *H. pylori* is present in a sample. The methods may comprise obtaining a threshold level of *H. pylori* DNA from the sample, amplifying a region of the *H. pylori* DNA to generate multiple copies of the region of the *H. pylori* DNA, sequencing the multiple copies of the region of the *H. pylori* DNA, comparing sequences of multiple copies of the region of the *H. pylori* DNA to a reference sequence, identifying the presence of a mutation in multiple copies of the region of the *H. pylori* DNA, and determining a number of the multiple copies of the region of the *H. pylori* DNA with the mutation, wherein antibiotic resistant *H. pylori* is present in the sample when the number of the multiple copies of the region of the *H. pylori* DNA with the mutation is above a predetermined amount.

15 Claims, 14 Drawing Sheets

Specification includes a Sequence Listing.

PCR primers.

| Pool | Amplicon | Amplicon size (bp) | PCR Primer Sequences (SEQ ID NO.) |
|---|---|---|---|
| rdxA-F1 | rdxA 188 | 188 | TGGTAATTGTTTCGTTAGGGAT (SEQ ID NO. 23)<br>TGGCGATTTCAGCGATTT (SEQ ID NO. 24) |
| | rdxA 156 | 156 | AAGCGCTTCAGCGTTAAT (SEQ ID NO. 25)<br>TGCATGCTGTGGTTGAAT (SEQ ID NO. 26) |
| | rdxA 177 | 177 | GAAGAGCGTATCAATAAGCCTAAA (SEQ ID NO. 27)<br>ATGCCACTCCTTGAACTTTAAT (SEQ ID NO. 28) |
| rdxA-F2 | rdxA-5-2-163 | 163 | AGCCTCCAATAATGCAACTATCC (SEQ ID NO. 29)<br>CATACCACCATTAACGCTGAAG (SEQ ID NO. 30) |
| | rdxA 182 | 182 | ATGCTTGGCGTGAGATTC (SEQ ID NO. 31)<br>GGCTTATTGATACGCTCTTCT (SEQ ID NO. 32) |
| rdxA-R1 | rdxA-R-150 | 150 | ATGCCACTCCTTGAACTTTA (SEQ ID NO. 33)<br>GCATGCTTGATCGCTTTG (SEQ ID NO. 34) |
| | rdxA-R-164 | 164 | ATGCAACTATCCAATCCCATTA (SEQ ID NO. 35)<br>CCGGAGTCTTATAAAGTTAGAGTG (SEQ ID NO. 36) |
| | rdxA-R-171 | 171 | GTGCGCTGCAATTTGTTT (SEQ ID NO. 37)<br>TTAAACGAGCGCCATTCTT (SEQ ID NO. 38) |
| rdxA-R2 | rdxA-R-187 | 187 | CAACCAAGTAATCGCATCAAC (SEQ ID NO. 39)<br>CATGGGCGTGAGCTTAAT (SEQ ID NO. 40) |
| | rdxA-R-174 | 174 | CTAACTTTATAAGACTCCGGATAGA (SEQ ID NO. 41)<br>TGTGATGGTTACTGATAAGGAT (SEQ ID NO. 42) |
| | rdxA-R-189 | 189 | CTGGCGATTTCAGCGATTT (SEQ ID NO. 43)<br>TGGTAATTGTTTCGTTAGGGAT (SEQ ID NO. 44) |

Figure 3A

| | | | |
|---|---|---|---|
| 5GF | 16SrRNA 168 | 168 | TAACGCATTAAGCATCC (SEQ ID NO. 1)<br>CCAGACACTCCACTATTT (SEQ ID NO. 2) |
| | 23SrRNA 194 | 194 | CCGACCTGCATGAAT (SEQ ID NO. 3)<br>AGCCAAAGCCCTTAC (SEQ ID NO. 4) |
| | gyrA 193 | 193 | TATGCGATGCATGAATTAG (SEQ ID NO. 5)<br>CATCAATAGAGCCAAAGTT (SEQ ID NO. 6) |
| | pbpA 159 | 159 | TTGATAATGGCTATTCC (SEQ ID NO. 7)<br>GGCTCAAGGCTTCTT (SEQ ID NO. 8) |
| | rpoB 228 | 228 | GACAAGCTCACTACCATGAG (SEQ ID NO. 9)<br>CACATCCCTGGCTTCAAA (SEQ ID NO. 10) |
| 5GR | 16SrRNA 162R | 162 | CTAGCGGATTCTCTCAA (SEQ ID NO. 11)<br>CAGTAATGCAGCTAACG (SEQ ID NO. 12) |
| | 23SrRNA 170R | 170 | CATCAAGGGTGGTATCT (SEQ ID NO. 13)<br>TTGTAGTGGAGGTGAAA (SEQ ID NO. 14) |
| | gyrA 139R | 139 | CGTTATCGCCATCAATAG (SEQ ID NO. 15)<br>GGTGATGTGATTGGTAAAT (SEQ ID NO. 16) |
| | gyrA 137R | 137 | CCATCAATAGAGCCAAAG (SEQ ID NO. 17)<br>ATCGTGGGTGATGTG (SEQ ID NO. 18) |
| | pbpA 140 | 140 | TTGATAATGGCTATTCC (SEQ ID NO. 19)<br>GGTTACAAGCCCTAAA (SEQ ID NO. 20) |
| | rpoB-R-167 | 167 | TGGGACAAATTCGGCCATAA (SEQ ID NO. 21)<br>TTTCATGGGCGGTCAGC (SEQ ID NO. 22) |

| | | |
|---|---|---|
| H.pylori diagnostic 23S rRNA amplicon | 125 | ACAACCCAGACTACCAAATAAG (SEQ ID NO. 45)<br>GTGAGCTGTTACGCTTTCT (SEQ ID NO. 46) |

Figure 3B

Reference sequences.

H. pylori 16S rRNA (SEQ ID NO. 47)

GTAATCCGTAGAGATCAAGAGGAATACTCATTGCGAGGCGACCTGCTGGAACATTACTGACGCTGATTGCG
CGAAAGCGTGGGGAGCAAACAGGATTAGATACCCTGGTAGTCCACGCCCTAAACGATGGATGCTAGTTGTT
GGAGGGCTTAGTTTTCCAGTAATGCAGCTAACGCATTAAGCATCCCGCCTGGGGAGTACGGTCGCAAGATT
AAAATCAAAGGAATAGACGGGGACCCGCACAAGCGGTGGAGCATGTGGTTTAATTCGAAGATACACGAAGA
ACCTTACCTAGGCTTGACATTGAGAGAATCCGCTAGAAATAGTGGAGTGTCTGGCTTGCCAGACCTTGAAA
ACAGGTGCTGCACGGCTGTCGTCAGCTCGTGTCGTGAGATGTTGGGTTAAGTCCCGCAACGAGCGCAACCC
CTTTTCTTAGTTGCTAACAGGTTATGCTGAGAACTCTAAGGATACTGCCTCCGTAAGGAGGAGGAAGGTGG
GGA

H. pylori 23S rRNA (SEQ ID NO. 48)

CAAGTGATAATAAAAGGGGGTAGAGCCCTGATTGGGCTAGGGCTGCTCGCCGCGGTACCAAACCCTATCA
AACTTCGAATACCTTTTATCGTATCTTGGGAGTCAGGCGGTGGGTGATAAAATCAATCGTCAAAAGGGGA
ACAACCCAGACTACCAAATAAGGTCCCTAAGTTCTATTCTGAGTGGAAAAAGATGTGTGGCTACTCAAAC
AACCAGGAGGTTGGCTTAGAAGCAGCCATCCTTTAAAGAAAGCGTAACAGCTCACTGGTCTAGTGGTCAT
GCGCTGAAAATATAACGGGGCTAAGATAGACACCGAATTTGTAGATTGTGTTAAACACAGTGGTAGAAGA
GCGTTCATACCAGCGTTGAAGGTATACCGGTAAGGAGTGCTGGAGCGGTATGAAGTGAGCATGCAGGAAT
GAGTAACGATAAGATATATGAATTGTATCCGCCGTAAATCTAAGGTTTCCTACGCGATGGTCGTCATC
GTAGGGTTAGTCGGGTCCTAAGCCGAGTCCGAAAGGGGTAGGTGATGGCAAATTGGTTAATATTCCAATA
CCGACTGTGGAGCGTGATGGGGGGACGCATAGGGTTAAGCGAGCTAGCTGATGGAAGCGCTAGTCTAAGG
GCGTAGATTGGAGGGAAGGCAAATCCACCTCTGTATTTGAAACCCAAACAGGCTCTTTGAGTCCTTTTAG
GACAAAGGGAGAATCGCTGATACCGTCGTGCCAAGAAAAGTCTCTAAGCATATCCATAGTCGTCCGTACC
GCAAACCGACACAGGTAGATGAGATGAGTATTCTAAGGCGCGTGAAAGAACTCTGGTTAAGGAACTCTGC
AAACTAGCACCGTAAGTTCGCGATAAGGTGTGCCACAGCGATGTGGTCTCAGCAAAGAGTCCCTCCCGAC
TGTTTACCAAAAACACAGCACTTTGCCAACTCGTAAGAGGAAGTATAAGGTGTGACGCCTGCCCGGTGCT
CGAAGGTTAAGAGGATGCGTCAGTCGCAAGATGAAGCGTTGAATTGAAGCCCGAGTAAACGGCGGCCGTA
ACTATAACGGTCCTAAGGTAGCGAAATTCCTTGTCGGTTAAATACCGACCTGCATGAATGGCGTAACGAG
ATGGGAGCTGTCTCAACCAGAGATTCAGTGAAATTGTAGTGGAGGTGAAAATTCCTCCTACCCGCGGCAA
GACGGAAAGACCCCGTGGACCTTTACTACAACTTAGCACTGCTAATGGGAATATCATGCGCAGGATAGGT
GGGAGGCTTTGAAGTAAGGGCTTTGGCTCTTATGGAGCCATCCTTGAGATACCACCCTTGATGTTTCTGT
TAGCTAACTGGCCTGTGTTATCCACAGGCAGGACAATGCTTGGTGGGTAGTTTGACTGGGGCGGTCGCCT
CCTAAAAAGTAACGGAGGCTTGCAAAGGTTGGCTCATTGCGGTTGGAAATCGCAAGTTGAGTGTAATGGC
ACAAGCCAGCCTGACTGTAAGACATACAAG

H. pylori gyrA (SEQ ID NO. 49)

ATGCAAGATAATTCAGTCAATGAAACAAAAAATATTGTAGAAGTGGGGATTGATTCTTCTATTGAAGAGA
GCTATTTAGCTTATTCCATGAGCGTGATCATAGGGCGCGCTTTACCGGACGCTAGAGATGGCTTAAAGCC
CGTGCATAGGCGTATTTTGTATGCGATGCATGAATTAGGCCTTACTTCAAAAGTCGCTTACAAAAAAAGC
GCTAGGATCGTGGGTGATGTGATTGGTAAATACCACCCCATGGCGATAATGCGGTTTATGATGCGCTAG
TGAGAATGGCGCAAGATTTTTCCATGCGTTTGGAATTAGTGGATGGGCAGGCAACTTTGGCTCTATTGA
TGGCGATAACGCCGCAGCGATGCGTTACACTGAAGCCAGAATGACTAAGGCGAGTGAAGAAATTTTAAGG
GATATTGATAAAGACACCATTGATTTTGTGCCTAATTATGACGATACCTTAAAAGAGCCAGATATTTTAC
CAAGCCGTCTGCCTAACCTTTTAGTCAATGGGGCTAATGGGATCGCTGTGGGGATGGCGA

Figure 3C

*H. pylori pbpA* (also known as pbp1) (SEQ ID NO. 50)

AACTAACGCGTCTAATGAAGATGAAGACAACTTAAACGCTAGCATGATCGTTACAGACACGAGCACCGGT
AAGATTTTAGCTTTAGTGGGGGGGATTGATTATAAAAAAGCGCTTTCAATCGCGCCACGCAAGCCAAAC
GGCAGTTTGGGAGCGCGATAAAGCCTTTTGTGTATCAGATCGCTTTTGATAATGGCTATTCCACGACTTC
TAAAATCCCTGATACCGCGCGAAACTTTGAAAATGGCAATTATAGTAAAAACAGTGAACAAAACCACGCA
TGGCACCCCAGCAATTATTCTCGCAAGTTTTTAGGGCTTGTAACCTTGCAAGAAGCCTTGAGCCATTCGT
TAAATCTAGCCACGATCAATTTAAGCGATCAGCTTGGCTTTGAAAAAATTTATCAATCTTTAAGCGATAT
GGGGTTTAAAAACCTCCCTAAGGACTTGTCTATTGTGTTAGGGAGCTTTGCTATCTCACCCATTGATGCA
GCTGAAAAGT

*H. pylori rpoB* (SEQ ID NO. 51)

ATGAAGATATTATCACCACCGTTAAATACCTCATGAAGATCAAAAACAATCAAGGCAAGATTGATGACAG
GGACCACTTGGGCAATCGTAGGATTAGGGCGGTAGGGGAATTGTTGGCCAATGAATTGCATTCAGGTTTA
GTGAAAATGCAAAAGACCATTAAAGACAAGCTCACTACCATGAGCGGGGCTTTTGATTCGCTCATGCCCC
ATGACTTGGTCAATTCTAAAATGATCACAAGCACCATCATGGAATTTTTCATGGGCGGTCAGCTCTCGCA
ATTTATGGATCAAACGAATCCCTTGAGTGAGGTTACGCACAAGCGCCGCCTTTCAGCGCTCGGCGAAGGG
GGGTTGGTGAAAGACAGAGTGGGGTTTGAAGCCAGGGATGTGCACCCCACGCATTATGGCCGAATTTGTC
CCATTGAGACCCCAGAAGGTCAAAATATCGGTCTGATCAACACCCTTTCCACTTTCACAAGAGTGAATGA
TTTAGGCTTTATTGAAGCCCCTTATAAAAAGGTTGTGGATGGCAAGGTCGTGGGTGAGACGATTTATTTG
ACCGCTATTCAAGAAGACAGCCACATCATCGCTCCCGCAA

*H. pylori rdxA* (SEQ ID NO. 52)

ATTTGAGCATGGGGCAGATTTTAAGCTTATTTATGGTAATTGTTTCGTTAGGGATTTTATTGTATGCTAC
AAAAAATTCTAAAAAAATAAAGGAAAATCAATGAAATTTTTGGATCAAGAAAAAGAAGACAATTATTAA
ACGAGCGCCATTCTTGCAAGATGTTTGATAGCCATTATGAGTTTTCTAGCACAGAATTAGAAGAAATCGC
TGAAATCGCCAGGCTATCGCCAAGCTCTTACAACACGCAGCCATGGCATTTTGTGATGGTTACTGATAAG
GATTTAAAAAAACAAATTGCAGCGCACAGCTATTTCAATGAAGAGATGATTAAAAGCGCTTCAGCGTTAA
TGGTGGTATGCTCTTTAAGACCCAGCGAGTTGTTACCACACGGCCACTACATGCAAAATCTCTATCCGGA
GTCTTATAAAGTTAGAGTGATCCCCTCTTTTGCTCAAATGCTTGGCGTGAGATTCAACCACAGCATGCAA
AGATTAGAAAGCTATATTTTAGAGCAATGCTATATCGCTGTGGGGCAAATTTGCATGGGCGTGAGCTTAA
TGGGATTGGATAGTTGCATTATTGGAGGCTTTGATCCTTTAAAGGTGGGCGAAGTTTTAGAAGAGCGTAT
CAATAAGCCTAAAATCGCATGCTTGATCGCTTTGGGCAAAGGGTGGCAGAAGCGAGTCAAAAATCAAGAA
AATCAAAAGTTGATGCGATTACTTGGTTGTGATTAAACAAAATCAAAAACTTTTTAACTATAATCAAACC
TAAATTAAAGTTCAAGGAGTGGCATTTTGTTTAAAAGAATGGTTTTAATCGCTCTTTTAGGGGTGTTTTC
AAGCGTTTCATTAAGCGCTAAGAGTCTTTTAAGAGATGATGGGATTTAGTCTCTGATTTAAAGGGCATG
AAATCAGAACTATCTGATGCTCCTGCTTGGGTTTTTGAAGACGCTAAAGCCCCCTACGAAGAAATGGGCG
TGGCGTATATCCCTGTTAATAATAAATATTTAGGGATTGAGCAAGCGACCTT

Figure 3D

| | | 16s rRNA- Tetracycline (Wild Type: AGA) | | 23s rRNA- Clarithromycin Wild Type AA | | gyrA-Fluoroquinolones* Wild type Amino Acids: NADA | | pbp-1a- Amoxycillin Wild Type: AGC | | rpoB-Rifampins Wild Type: No amino acid change in Codon 524-545 | | rdxA_ Metronidazole ** Wild type: No truncation | |
|---|---|---|---|---|---|---|---|---|---|---|---|---|---|
| | Sample ID | NGS | Sanger Sequencing | NGS | Sanger Sequencing | NGS | Sanger Sequencing | NGS | Sanger Sequencing | NGS | Sanger Sequencing | NGS | Sanger Sequencing |
| 1 | FFPE_B | Wt | | Wt | | ACC(p.N>T) | ACC(p.N>T) | Wt | | Wild Type | | Wild Type | |
| 2 | FFPE_BB | Wt | | Wt | | ACC(p.N>T) | ACC(p.N>T) | Wt | | Wild Type | | Wild Type | |
| 3 | FFPE_C | Wt | Wt | Wt | Wt | CCG(p.A>P) AAT(p.D>N) | CCG(p.A>P) AAT(p.D>N) | Wt | Wt | Wild Type | Wild Type | Wild Type | |
| 4 | FFPE_D | Wt | | Wt | | Wild Type | Wild Type | Wt | Wt | Wild Type | Wild Type | Wild Type | |
| 5 | FFPE_E | Wt | | Wt | | ACC(p.N>T) | ACC(p.N>T) | Wt | | Wild Type | | Wild Type | |
| 6 | FFPE_F | Wt | | Wt | | Wild Type | | Wt | | Wild Type | | Wild Type | |
| 7 | FFPE_H | Wt | | Wt | | ACC(p.N>T) | ACC(p.N>T) | Wt | | Wild Type | | Wild Type | |
| 8 | FFPE_I | Wt | | Wt | | Wild Type | | Wt | | Wild Type | | Wild Type | |
| 9 | FFPE_J | Wt | | Wt | | AA/CC(p.N>N/T) G/AAT(p.D>D/N) | AA/CC(p.N>N/T) G/AAT(p.D>D/N) | Wt | | Wild Type | | INS AG | INS AG |
| 10 | FFPE_K | Wt | | Wt | Wt | GTG(p.D>V) | GTG(p.D>V) | Wt | | Wild Type | | Wild Type | |
| 11 | FFPE_L | Wt | | AG | AG | Wild Type | | Wt | | Wild Type | | Wild Type | |
| 12 | FFPE_O | Wt | Wt | GA | GA | ATT(p.N>I) | ATT(p.N>I) | Wt | Wt | Wild Type | Wild Type | Wild Type | |
| 13 | FFPE_Q | Wt | Wt | AG | AG | Wild Type | Wild Type | Wt | Wt | Wild Type | Wild Type | INS G | INS G |
| 14 | FFPE_R | Wt | Wt | Wt | Wt | Wild Type | Wild Type | Wt | Wt | Wild Type | Wild Type | DEL 11bp | DEL 11bp |
| 15 | FFPE_S | Wt | Wt | Wt | | GGT(p.D>G) | GGT(p.D>G) | Wt | Wt | Wild Type | | Wild Type | |
| 16 | FFPE_T | Wt | Wt | Wt | | AAT(p.D>N) | AAT(p.D>N) | Wt | Wt | Wild Type | | Wild Type | |
| | Wt: Wild Type | | | | | * mutations in nucleotide codon sequence are underlined with corresponding protein change in amino acid in parenthesis. | | | | | | | |
| | | | | | | Amino acid codes: N- Asparagine, A: Alanine, D: Aspartic Acid, T: Tyrosine, P: Proline, I: Isoleucine, V: Valine, G:Glycine | | | | | | | |
| | | | | | | ** insertions or deletions in rdxA listed result in truncated protein resulting in Metronidazole resistance. | | | | | | | |

Figure 6

| NO | Sample ID | Antibiotic Gene Mutation | Mutation Frequency |
|---|---|---|---|
| 1 | B | 23S rRNA (A2143G) | 31.6% |
| | | gyrA (Asp91Asn) | 5.9% |
| 2 | BB | gyrA (Asp91Asn) | 9.4% |
| 3 | C | 23S rRNA (A2143G) | 34.8% |
| | | gyrA (Asp91Asn) | 97% |
| 4 | D | gyrA (Asp91Asn) | 35% |
| 5 | E | No mutation detected | |
| 6 | F | No mutation detected | |
| 7 | G | rdxA (Glu75*) | 16.8% |
| | | rdxA (Gln6*) | 18.6% |
| 8 | H | No mutation detected | |
| 9 | I | No mutation detected | |
| 10 | J | gyrA (Asp91Asn) | 44.8% |
| | | rdxA (Gln6*) | 7.6% |
| 11 | K | 23S rRNA (A2143G) | 42% |
| 12 | L | 23S rRNA (A2143G) | 87.8% |
| 13 | M | No mutation detected | |
| 14 | O | 23S rRNA (A2142G) | 87% |
| 15 | P | gyrA (Asp91Asn) | 5.6% |
| 16 | Q | 23S rRNA (A2143G) | 90% |
| 17 | R | No mutation detected | |
| 18 | S | gyrA (Asp91Gly) | 96.3% |
| 19 | T | gyrA (Asn87Lys) | 99.4% |
| | | gyrA (Asp91Asn) | 66.8% |
| 20 | U | rdxA (Glu75*) | 6.4% |
| 21 | V | No mutation detected | |
| 22 | W | No mutation detected | |
| 23 | X | No mutation detected | |
| 24 | Z | No mutation detected | |

Figure 7

Study report generated from various mixing experiments using DNA samples containing two or three samples with different antibiotic resistance strains

Mixed Strain Studies

| Combination | Sample ID | 23S rRNA | | gyrA | | rdxA | | 16S rRNA | |
|---|---|---|---|---|---|---|---|---|---|
| | 1002 | A2143G | 99.40% | A272G Asp91Gly | 99.40% | | | T926C | 99.50% |
| | | | | | | | | C927A | 98.80% |
| | | | | | | | | T928G | 99.30% |
| | 1025 | | | | | pGlu194* | 50.70% | | |
| | | | | | | G352A | 99.60% | | |
| Combination 1 | 1002 + 1025 | A2143G | 47.10% | A272G Asp91Gly | 42.30% | pGlu194* | 28.10% | T926C | 51.50% |
| | | | | | | G352A | 62.90% | C927A | 51.20% |
| | | | | | | | | T928G | 51.30% |
| | 1645 | A2143G | 6.20% | G271A Asp91Asn | 99.80% | pCys87* | 13.50% | | |
| | | | | | | G352A | 99.60% | | |
| Combination 2 | 1002 + 1025 + 1645 | A2143G | 25.20% | G271A Asp91Asn | 49% | pGlu194* | 17.40% | T926C | 30.90% |
| | | | | A272G Asp91Gly | 21% | pCys87* | 8.90% | C927A | 30.70% |
| | | | | | | G352A | 85.50% | T928G | 30.80% |
| | DG-1014 | | | | | pR41Rfs | 47.30% | | |
| | DG-1008 | A2142G | 99.70% | G271A Asp91Asn | 99.70% | | | | |
| Combination 3 | 1014 + 1008 | A2142G | 57.80% | G271A Asp91Asn | 80.20% | pR41Rfs | 14.20% | | |

Figure 8

Representation of detection results and quantitation threshold and interpretation of antibiotic resistance in one gene

| Reads | 23S rRNA Frequency | Mix strain or not |
|---|---|---|
| 500 | 100% | One strain w/ Clarithromycin resistance |
| 500 | 98% | One strain w/ Clarithromycin resistance |
| 500 | 95 | Likely one strain w/ Clarithromycin resistance |
| 500 | 90 | Mix strains |
| 500 | 50 | Mix strains |
| 500 | 20 | Mix strains |
| 500 | 10 | Mix strains |
| 500 | 5 | Likely wildtype |
| 500 | Less than 5 | Wildtype |

If only 23S rRNA gene mutation found in this patient sample

Figure 10A

Representation of detection results and quantitation threshold and interpretation of antibiotic resistance in two genes

| Reads | 23S rRNA Frequency | gyrA Frequency | Mix strain or not |
|---|---|---|---|
| 500 | 100% | 100% | One strain w/Clarithromycin and Fluoroquinolones resistances |
| 500 | 98% | 98% | One strain w/Clarithromycin and Fluoroquinolones resistances |
| 500 | 95 | 95 | Likely one strain w/Clarithromycin and Fluoroquinolones resistances |
| 500 | 90 | 70 | Mix strains* |
| 500 | 80 | 60 | Mix strains* |
| 500 | 70 | 50 | Mix strains* |
| 500 | 60 | 40 | Mix strains* |
| 500 | 50 | 30 | Mix strains* |
| 500 | 30 | 20 | Mix strains* |
| 500 | 20 | 10 | Mix strains* |
| 500 | 10 | 5 | Mix strains* |
| 500 | 5 | 5 | Mix strains* |
| 500 | Less than 5 | Less than 5 | Wildtype |

If 23S rRNA and gryA are mutated

Note*
possible strains w/ Clarithromycin + Fluoro +
possible strains w/ Clarithromycin - Fluoro +
possible strains w/ Clarithromycin + Fluoro -
possible strains w/ wildtype

Figure 10B

Representation of detection results and quantitation threshold and interpretation of antibiotic resistance in multiple genes

| Reads | 23SrRNA Frequency | gyrA Frequency | rdxA Frequency | Mix strain or not |
|---|---|---|---|---|
| 500 | 100% | 100% | 100% | One strain w/Clarithromycin, Fluoroquinolones and Metronidazole resistances |
| 500 | 98% | 98% | 98% | Likely one strain w/Clarithromycin, Fluoroquinolones and Metronidazole resistances |
| 500 | 95 | 95 | 95 | Likely one strain w/Clarithromycin, Fluoroquinolones and Metronidazole resistances |
| 500 | 90 | 90 | 90 | Mix strains* |
| 500 | 70 | 50 | 50 | Mix strains* |
| 500 | 60 | 40 | 70 | Mix strains* |
| 500 | 50 | 50 | 60 | Mix strains* |
| 500 | 40 | 40 | 50 | Mix strains* |
| 500 | 30 | 40 | 40 | Mix strains* |
| 500 | 20 | 20 | 20 | Mix strains* |
| 500 | 10 | 10 | 10 | Mix strains* |
| 500 | 5 | 5 | 5 | Mix strains* |
| 500 | Less than 5 | Less than 5 | Less than 5 | Wildtype |

If DNA variants detected in all 23S rRNA, gyrA and rdxA genes

Note*
possible strains w/ Clarithromycin + Fluoro + Metronidazole +
possible strains w/ Clarithromycin + Fluoro - Metronidazole +
possible strains w/ Clarithromycin + Fluoro - Metronidazole -
possible strains w/ Clarithromycin + Fluoro +Metronidazole -
possible strains w/ Clarithromycin - Fluoro + Metronidazole +
possible strains w/ Clarithromycin - Fluoro - Metronidazole +
possible strains w/ Clarithromycin - Fluoro + Metronidazole -
possible strains w/ wildtype

Figure 10C

METHODS FOR DETECTION OF ANTIBIOTIC RESISTANT *H. PYLORI*

CROSS-REFERENCE TO RELATED APPLICATIONS

This application is the national stage of International Patent Application No. PCT/US2018/061439, filed Nov. 16, 2018, which claims the benefit of and priority to U.S. patent application Ser. No. 62/587,097, filed Nov. 16, 2017, each of which are incorporated herein by reference in their entirety.

FIELD

The present disclosure generally provides methods and materials for detection of antibiotic resistant *Helicobacter pylori* (*H. pylori*).

STATEMENT REGARDING SEQUENCE LISTING

The Sequence Listing associated with this application is provided in text format in lieu of a paper copy, and is hereby incorporated by reference into the specification. The name of the text file containing the Sequence Listing is 116110_5003_US_Sequence_Listing_ST25.txt. The text file is about 18.0 KB, was created on Dec. 23, 2022, and is being submitted electronically via EFS-Web.

BACKGROUND

*H. pylori* is one of the most prevalent global human pathogens that infects an estimated 50% of the world's population. *H. pylori* is primarily found in the stomach and plays an important role in the pathogenesis of chronic gastritis, peptic ulcers, mucosa-associated lymphoid tissue (MALT) lymphoma, gastric carcinoma, and gastric cancer. *H. pylori* also plays an important role in pathogenesis unrelated to intestinal diseases, including: immune thrombocytopenic purpura, refractory iron deficiency anemia, and B12 deficiency.

*H. pylori* infections or pathogenesis are treated with antibiotics. In fact, the front line therapy for treating *H. pylori* infections or pathogenesis usually involves triple antibiotic therapy, comprising administering a proton-pump inhibitor (PPI) and two more antibiotics, such as clarithromycin and either metronidazole or amoxicillin. However, this type of therapy is only effective if the *H. pylori* being targeted is not clarithromycin resistant or resistant to metronidazole or penicillin-like drugs such as amoxicillin. Other antibiotics may be used, but in each case it is critical to know whether the *H. pylori* strain afflicting the patient is resistant to any particular antibiotic to provide effective therapeutic treatment.

Drug resistant and multi-drug resistant strains of *H. pylori* are becoming increasingly common, causing a decrease in antimicrobial *H. pylori* eradication rates. Because of this, it is critical that a treatment therapy be selected based on pretreatment antibiotic susceptibility testing. Unfortunately, this strategy has not been practical due to the lack of available rapid and reliable antibiotic resistance tests.

Traditional methods of detecting *H. pylori* antibiotic resistance have serious disadvantages. For example, such methods are only capable of testing a single *H. pylori* strain and thus may fail to provide complete antimicrobial resistance data. This is particularly true in regions with high *H. pylori* infection rates where patients are more likely to be infected with multiple strains of *H. pylori*. Additionally, these methods require culturing *H. pylori*, which is tedious and has a high frequency of failure due to sampling bias and poor sample preservation during shipment. Thus, there is a need for a faster, more reliable, non-invasive test to determine *H. pylori* antibiotic resistance.

SUMMARY

The present disclosure relates to methods and materials for detection of antibiotic resistant strains of *Helicobacter pylori* (*H. pylori*) in a sample including, for example, detection of antibiotic resistant strains of *H. pylori* among mixed strains of *H. pylori*. Additionally, the present disclosure relates to methods for obtaining *H. pylori* DNA from a sample.

The present disclosure provides methods and materials for determining if antibiotic resistant *H. pylori* (e.g., one or more strains of antibiotic resistant *H. pylori*) is present in a sample. The methods may comprise: obtaining a threshold level of *H. pylori* DNA from the sample, amplifying a region of the *H. pylori* DNA to generate multiple copies of the region of the *H. pylori* DNA, sequencing the multiple copies of the region of the *H. pylori* DNA, comparing sequences of multiple copies of the region of the *H. pylori* DNA to a reference sequence, identifying the presence of a mutation in multiple copies of the region of the *H. pylori* DNA, and determining a number of the multiple copies of the region of the *H. pylori* DNA with the mutation, wherein antibiotic resistant *H. pylori* is present in the sample when the number of the multiple copies of the region of the *H. pylori* DNA with the mutation is above a predetermined amount. In a further embodiment, the number of the multiple copies of the region of the *H. pylori* DNA with the mutation is above a predetermined amount where the region of the *H. pylori* DNA with the mutation is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98% or greater of the sequenced multiple copies of the region of the *H. pylori* DNA.

In some embodiments of each or any of the above or below mentioned embodiments, the threshold level of *H. pylori* DNA is DNA from at least 10 *H. pylori* genomes (e.g., the amount of DNA present in at least 10 *H. pylori* genomes). In another embodiment, the threshold level of *H. pylori* DNA is DNA from at least 50 fragments of *H. pylori* DNA. In yet another embodiment, the threshold level of *H. pylori* DNA is DNA from between 50 and 100 fragments of *H. pylori* DNA.

In some embodiments of each or any of the above or below mentioned embodiments, the sample is a biopsy sample and, in another embodiment, the biopsy is a dental plaque, gastric juice, or gastric biopsy. In a further embodiment, the biopsy sample is formalin fixed or formalin-fixed and paraffin embedded (FFPE).

In some embodiments of each or any of the above or below mentioned embodiments, the method further comprises the step of providing one or more wild-type gene sequences or reference sequences corresponding to the amplified regions of *H. pylori* DNA.

In some embodiments of each or any of the above or below mentioned embodiments, the mutation in the multiple copies of the region of the *H. pylori* DNA is detected by next generation sequencing (NGS).

In some embodiments of each or any of the above or below mentioned embodiment, the steps of amplifying and sequencing the one or more regions of *H. pylori* DNA comprises: identifying PCR primer pairs suitable for producing amplicons comprising the one or more regions of the *H. pylori* DNA; segregating PCR primer pairs comprising one or more primers that interfere with amplicon generation by another PCR primer pair into separate PCR primer pair pools, wherein each of the separate PCR primer pair pools contain a plurality of PCR primer pairs; generating amplicons from each of the separate PCR primer pair pools and the *H. pylori* DNA; and combining all amplicons produced from each of the separate PCR primer pair pools and the *H. pylori* DNA into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different samples, and sequencing all indexed sample amplicons simultaneously. In an embodiment, the method further comprises the step of identifying mutations within the indexed sequence amplicons from a sample by reference to corresponding wild type gene sequences (e.g., a reference sequence).

In an embodiment, the PCR primer pairs are directed to one or more of the following genes: 16S rRNA (related to tetracycline resistance), 23S rRNA (related to clarithromycin resistance), pbp1 (related to resistance to penicillin antibiotics), gyrA (related to resistance to fluoroquinone antibiotics), rpoB (related to rifabutin resistance) and rdxA (involved in resistance to metronidazole).

In some embodiments of each or any of the above or below mentioned embodiments, the region of the *H. pylori* DNA comprises one or more *H. pylori* genes selected from the group comprising: 23S rRNA, gyrA, rdxA, frxA, pbp1, 16S rRNA, and rpoB. In another embodiment, the one or more identified mutations in the multiple copies of the one or more amplified regions of *H. pylori* DNA are selected from the group comprising: A2143G and A2142G mutations in 23S rRNA; A272G Asp91Gly and G271A Asp91Asn in gyrA; pGlu194, G352A, pCys87, pR41Rfs in rdxA; and T926C and C927A in 16A rRNA.

In some embodiments of each or any of the above or below mentioned embodiments, the identified mutation is an A2142G, A2143G, and/or A2142C mutation of the *H. pylori* 23S rRNA gene; an A928C, AG926-927GT, A926G/A928C and/or AGA926-928TTC mutation of the *H. pylori* 16S rRNA gene; a C261A, C261G, G271A, and/or G271T mutation of the *H. pylori* gyrA gene encoding DNA gyrase subunit A; between codons 525 and 545 of the *H. pylori* rpoB gene encoding the beta/beta' subunit of DNA-directed RNA polymerase; a C1242A or C1242G mutation in the *H. pylori* pbp1 gene encoding penicillin-binding protein 1; or within the *H. pylori* rdxA gene. In another embodiment, the identified mutation produces a loss of function of *H. pylori* oxygen-insensitive (Type I) NAPD(P)H nitroreductase encoded by rdxA.

In some embodiments of each or any of the above or below mentioned embodiments, the antibiotic resistance *H. pylori* is resistant to one or more of the following: macrolides, metronidazole, quinolones, rifamycins, amoxicillin, and tetracycline.

In some embodiments of each or any of the above or below mentioned embodiments, the sample is a fecal sample. In other embodiments, the fecal sample is obtained by the method comprising: exposing a first part of the fecal sample to an anti-*H. pylori* antibody, separating *H. pylori* bound to the anti-*H. pylori* antibody from fecal material in the first part of the fecal sample, extracting *H. pylori* DNA from the *H. pylori* separated from the first fecal material, exposing a second part of the fecal sample to a DNA probe that binds to *H. pylori* DNA, extracting the *H. pylori* DNA from the second part of the fecal sample, and pooling the *H. pylori* DNA obtained from the first part of the fecal sample and the *H. pylori* DNA obtained from the second part of the fecal sample.

The present disclosure also provides methods and materials for obtaining *H. pylori* DNA from a fecal sample, the method comprising: exposing a first part of the fecal sample to an anti-*H. pylori* antibody, separating *H. pylori* bound to the anti-*H. pylori* antibody from fecal material in the first part of the fecal sample, extracting *H. pylori* DNA from the *H. pylori* separated from the first fecal material, exposing a second part of the fecal sample to a DNA probe that bind to *H. pylori* DNA, extracting the *H. pylori* DNA from the second part of the fecal sample, and pooling the *H. pylori* DNA obtained from the first part of the fecal sample and the *H. pylori* DNA obtained from the second part of the fecal sample.

In some embodiments of each or any of the above or below mentioned embodiments, the method for obtaining *H. pylori* DNA from a fecal sample further comprises the step of homogenizing the fecal sample. In another embodiment, the anti-*H. pylori* antibody is labeled. In yet another embodiment, the anti-*H. pylori* antibody is labeled with biotin.

The present disclosure also provides methods and materials for treating *H. pylori* infection in a subject, the method comprising: obtaining a sample from the subject, obtaining a threshold level of *H. pylori* DNA from the sample, amplifying a region of the *H. pylori* DNA to generate multiple copies of the region of the *H. pylori* DNA, sequencing the multiple copies of the region of the *H. pylori* DNA, comparing sequences of the multiple copies of the region of the *H. pylori* DNA to one or more reference sequences, detecting a mutation in the multiple copies of the region of *H. pylori* DNA, determining a number of the multiple copies of the region of the *H. pylori* DNA with the mutation, wherein antibiotic resistant *H. pylori* is present in the sample when the number of the multiple copies of the region of the *H. pylori* DNA with the mutation is above a predetermined amount, and administering to the subject one or more antibiotics to which the *H. pylori* lacks resistance when antibiotic resistant *H. pylori* is present in the sample.

BRIEF DESCRIPTION OF THE DRAWINGS

FIGS. 3A-3B are tables of the individual primers disclosed in the Descriptions and Examples. FIGS. 3C-3D are reference sequences of *H. pylori* genes discussed herein.

FIG. 6 is a summary data table of 16 FFPE samples analyzed by Next Generation Sequencing (NGS) data from 16 FFPE samples using the segregational pooling and pooled amplicon strategy with mutations in each of six different genes characteristic of drug-resistant *H. pylori* identified. All mutations identified by NGS were confirmed by Sanger sequencing.

FIG. 7 is a summary data table of 24 FFPE samples analyzed by NGS data from 24 FFPE samples using the segregational pooling and pooled amplicon strategy with mutation in each of six different genes characteristic of drug-resistant *H. pylori* identified. The data table lists the gene mutations identified by NGS as well as their mutation frequency.

FIG. 8 is a summary data table of the analysis of *H. pylori* DNA samples containing a mixture of different antibiotic resistant strains.

FIG. 10A is a summary data table of the detection of a mutation in the 23S rRNA *H. pylori* gene and whether the detection of a mutation indicates mixed *H. pylori* strains. The data table lists the number of amplifications or "reads" of a sample from next generation sequencing, the number of the multiple copies of the region of the *H. pylori* DNA with a mutation, and whether the number of the multiple copies of the region of the *H. pylori* DNA with a mutation indicates the presence of antibiotic resistant *H. pylori*.

FIG. 10B is a summary data table of the detection of a mutation in the 23S rRNA and gyrA *H. pylori* genes and whether the detection of one or more mutations indicates mixed *H. pylori* strains. The data table lists the number of amplifications or "reads" of a sample from next generation sequencing, the number of the multiple copies of the region of the *H. pylori* DNA with a mutation, and whether the number of the multiple copies of the region of the *H. pylori* DNA with a mutation indicates the presence of antibiotic resistant *H. pylori*.

FIG. 10C is a summary data table of the detection of a mutation in the 23S rRNA, gyrA, and rdxA *H. pylori* genes and whether the detection of one or more mutations indicates mixed *H. pylori* strains. The data table lists the number of amplifications or "reads" of a sample from next generation sequencing, the number of the multiple copies of the region of the *H. pylori* DNA with a mutation, and whether the number of the multiple copies of the region of the *H. pylori* DNA with a mutation indicates the presence of antibiotic resistant *H. pylori*.

DETAILED DESCRIPTION

Figure 1:
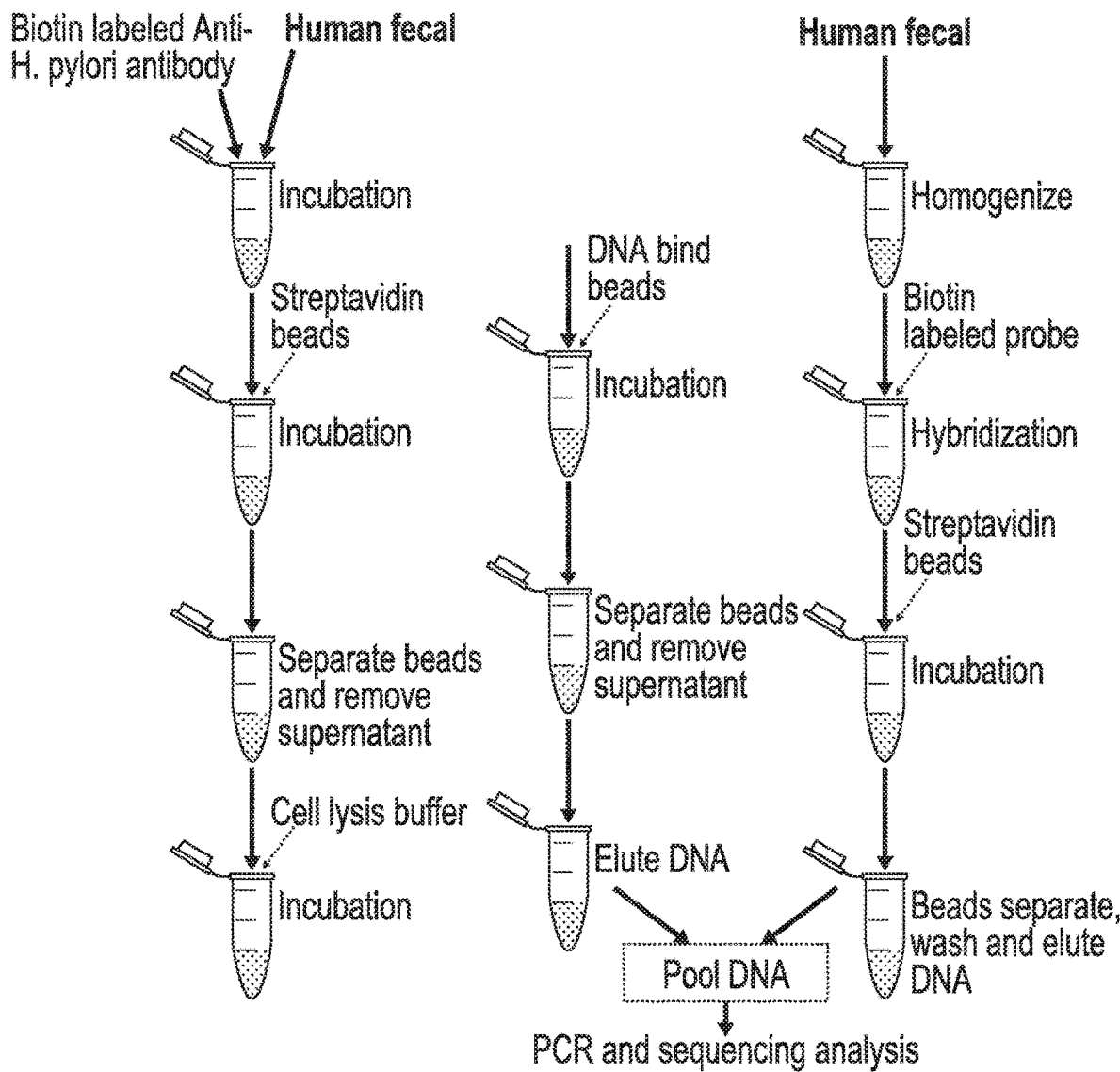
FIG. 1 is a flow chart depicting a method for obtaining *H. pylori* DNA from a fecal sample.

The ability to obtain information regarding *H. pylori* antibiotic resistance is critical to the effective, efficient treatment of *H. pylori* infections. This is particularly important given the increased prevalence of antibiotic resistant *H. pylori*. By identifying which antibiotic or antibiotics are not likely to work on a subject's *H. pylori* infection, subjects can receive personalized treatment of their infections. However, it is difficult to obtain a sufficient quantity and quality of *H. pylori* DNA from a patient sample (e.g., a biological sample) to conduct genetic analyses to assess whether *H. pylori* present in a sample is or is not sensitive to an antibiotic. The inventors have surprisingly found that a sufficient quantity (e.g., amount) of *H. pylori* DNA can be obtained from a sample such as a fecal sample by exposing a first part of the fecal sample to an anti-*H. pylori* antibody, separating *H. pylori* bound to the anti-*H. pylori* antibody from fecal material in the first part of the fecal sample, extracting *H. pylori* DNA from the *H. pylori* separated from the first fecal material, exposing a second part of the fecal sample to a DNA probe that binds to *H. pylori* DNA, extracting the *H. pylori* DNA from the second part of the fecal sample, and pooling the *H. pylori* DNA obtained from the first part of the fecal sample and the *H. pylori* DNA obtained from the second part of the fecal sample. Subsequently, *H. pylori* DNA obtained from a sample such as a fecal sample can be used to determine if antibiotic resistant *H. pylori* (e.g., one or more strains of antibiotic resistant *H. pylori*) is present in a sample.

The present disclosure provides methods for determining if antibiotic resistant *H. pylori* is present in a sample including, for example, a fecal sample. The methods may comprise: obtaining a threshold level of *H. pylori* DNA from the sample (e.g., DNA from at least 10 *H. pylori* genomes, at least 50 fragments of *H. pylori* DNA including, for example, between 50 and 100 fragments of *H. pylori* DNA), amplifying a region of the *H. pylori* DNA to generate multiple copies of the region of the *H. pylori* DNA, sequencing the multiple copies of the region of the *H. pylori* DNA, comparing sequences of the multiple copies of the region of the *H. pylori* DNA to a wild-type genetic sequence or a reference sequence, identifying the presence of a mutation in the multiple copies of the region of the *H. pylori* DNA, and determining a number of the multiple copies of the region of the *H. pylori* DNA with the mutation, wherein antibiotic resistant *H. pylori* is present in the sample when the number of the multiple copies of the region of the *H. pylori* DNA with the mutation is above a predetermined amount (e.g., the region of the *H. pylori* DNA with the mutation is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98% or greater of the sequenced multiple copies of the region of the *H. pylori* DNA).

In some embodiments of each or any of the above or below mentioned embodiments, the methods may further comprise: providing one or more wild-type genetic sequences or reference sequences of the amplified regions of *H. pylori* DNA. In other embodiments, the steps of amplifying and sequencing the one or more regions of *H. pylori* DNA may further comprise: identifying PCR primer pairs suitable for producing amplicons comprising the one or more regions of the *H. pylori* DNA; segregating PCR primer pairs comprising one or more primers that interfere with amplicon generation by another PCR primer pair into separate PCR primer pair pools, wherein each of the separate PCR primer pair pools contain a plurality of PCR primer pairs; generating amplicons from each of the separate PCR primer pair pools and the *H. pylori* DNA; and combining all amplicons produced from each of the separate PCR primer pair pools and the *H. pylori* DNA into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different samples, and sequencing all indexed sample amplicons simultaneously.

In some embodiments, the sample is a fecal sample. In further embodiments, the fecal sample may be obtained by methods comprising: exposing a first part of the fecal sample to an anti-*H. pylori* antibody, separating *H. pylori* bound to the anti-*H. pylori* antibody from fecal material in the first part of the fecal sample, extracting *H. pylori* DNA from the *H. pylori* separated from the first fecal material, exposing a second part of the fecal sample to a DNA probe that binds to *H. pylori* DNA, extracting the *H. pylori* DNA from the second part of the fecal sample, and pooling the *H. pylori* DNA obtained from the first part of the fecal sample and the

*H. pylori* DNA obtained from the second part of the fecal sample. In certain embodiments, the first part of the fecal sample is the same as the second part of the fecal sample.

The present disclosure also provides methods for obtaining *H. pylori* DNA from a sample, such as a fecal sample. The methods may comprise: exposing a first part of the fecal sample to an anti-*H. pylori* antibody, separating *H. pylori* bound to the anti-*H. pylori* antibody from fecal material in the first part of the fecal sample, extracting *H. pylori* DNA from the *H. pylori* separated from the first fecal material, exposing a second part of the fecal sample to a DNA probe that binds to *H. pylori* DNA, extracting the *H. pylori* DNA from the second part of the fecal sample, and pooling the *H. pylori* DNA obtained from the first part of the fecal sample and the *H. pylori* DNA obtained from the second part of the fecal sample. In certain embodiments, the first part of the fecal sample is the same as the second part of the fecal sample.

The present disclosure further provides methods for treating *H. pylori* infection in a subject. The methods may comprise: obtaining a sample from the subject, obtaining a threshold level of *H. pylori* DNA from the sample (e.g., DNA from at least 10 *H. pylori* genomes, at least 50 fragments of *H. pylori* DNA including, for example, between 50 and 100 fragments of *H. pylori* DNA), amplifying a region of the *H. pylori* DNA to generate multiple copies of the amplified region of the *H. pylori* DNA, sequencing the multiple copies of the region of the *H. pylori* DNA, comparing sequences of the multiple copies of the region of the *H. pylori* DNA to one or more reference sequences, detecting a mutation in the multiple copies of the region of *H. pylori* DNA, determining a number of the multiple copies of the region of the *H. pylori* DNA with the mutation, wherein antibiotic resistant *H. pylori* is present in the sample when the number of the multiple copies of the region of the *H. pylori* DNA with the mutation is above a predetermined amount (e.g., the region of the *H. pylori* DNA with the mutation is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98% or greater of the sequenced multiple copies of the region of the *H. pylori* DNA), and administering to the subject one or more antibiotics to which the *H. pylori* lacks resistance when antibiotic resistant *H. pylori* is present in the sample.

Obtaining *H. pylori* DNA from a Sample

The present disclosure provides methods for obtaining *H. pylori* DNA from a sample, such as a fecal sample, a dental plaque, dental saliva, gastric juice, or a gastric biopsy. In an embodiment where the sample is a fecal sample, such methods may comprise: exposing the fecal sample to an anti-*H. pylori* antibody, separating *H. pylori* bound to the anti-*H. pylori* antibody from fecal material in the fecal sample, and extracting *H. pylori* DNA from the *H. pylori* separated from the fecal material. The methods can be used to obtain DNA from a sample comprising intact and/or coccoid *H. pylori* (*H. pylori* body).

A fecal sample may be exposed to an anti-*H. pylori* antibody that, in a preferred embodiment, is labeled including, for example, with biotin. In a further preferred embodiment, the fecal sample may be homogenized. A biotin labeled anti-*H. pylori* antibody and the fecal sample may then be incubated using standard conditions for a period of time sufficient for the labeled anti-*H. pylori* antibody to bind intact and/or coccoid *H. pylori*. *H. pylori* bound to the labeled anti-*H. pylori* antibody may be separated from the fecal sample by incubating the fecal sample (comprising fecal material and *H. pylori* bound to the labeled anti-*H. pylori* antibody) with beads capable of binding to the labeled anti-*H. pylori* antibody such as streptavidin beads. *H. pylori* bound to the labeled anti-*H. pylori* antibody may then be separated from the fecal material in the fecal sample by separating the beads from the fecal material and removing any liquid or debris. *H. pylori* DNA may then be extracted from the *H. pylori* separated from the fecal material by incubating the *H. pylori* obtained from the fecal sample with a cell lysis buffer. The exposed *H. pylori* DNA may subsequently be incubated with beads for a period of time. The *H. pylori* DNA binds to the beads, such as through its binding to the anti-*H. pylori* antibody. The beads are separated from the lysis buffer or supernatant and the supernatant is removed. The *H. pylori* DNA may then be removed from the beads using an elution buffer.

Additionally, or alternatively, methods for obtaining *H. pylori* DNA from a fecal sample may comprise: exposing the fecal sample to a DNA probe that binds to *H. pylori* DNA (e.g., a nucleic acid fragment that is capable of hybridizing to the *H. pylori* DNA), and extracting the *H. pylori* DNA from the fecal sample. Such probes may be used to bind genomic and/or fragmented *H. pylori* DNA from the fecal sample. In a preferred embodiment, the DNA probe is a biotin labeled probe. Beads may be added to the DNA probe and fecal sample and then incubated for a period of time. In a preferred embodiment, the beads are streptavidin beads. In an embodiment, the beads are separated from the fecal sample and DNA probe, washed, and the *H. pylori* DNA eluted.

Both of the aforementioned methods may be combined as disclosed in FIG. 1 and may comprise: exposing a first part of the fecal sample to an anti-*H. pylori* antibody, separating *H. pylori* bound to the anti-*H. pylori* antibody from fecal material in the first part of the fecal sample, extracting *H. pylori* DNA from the *H. pylori* separated from the first fecal material, exposing a second part of the fecal sample to a DNA probe that binds to *H. pylori* DNA, extracting the *H. pylori* DNA from the second part of the fecal sample, and pooling the *H. pylori* DNA obtained from the first part of the fecal sample and the *H. pylori* DNA obtained from the second part of the fecal sample. In a preferred embodiment, *H. pylori* DNA collected from each method is pooled for subsequent PCR and sequencing analysis. In certain embodiments, the first part of the fecal sample is the same as the second part of the fecal sample.

Figure 2:
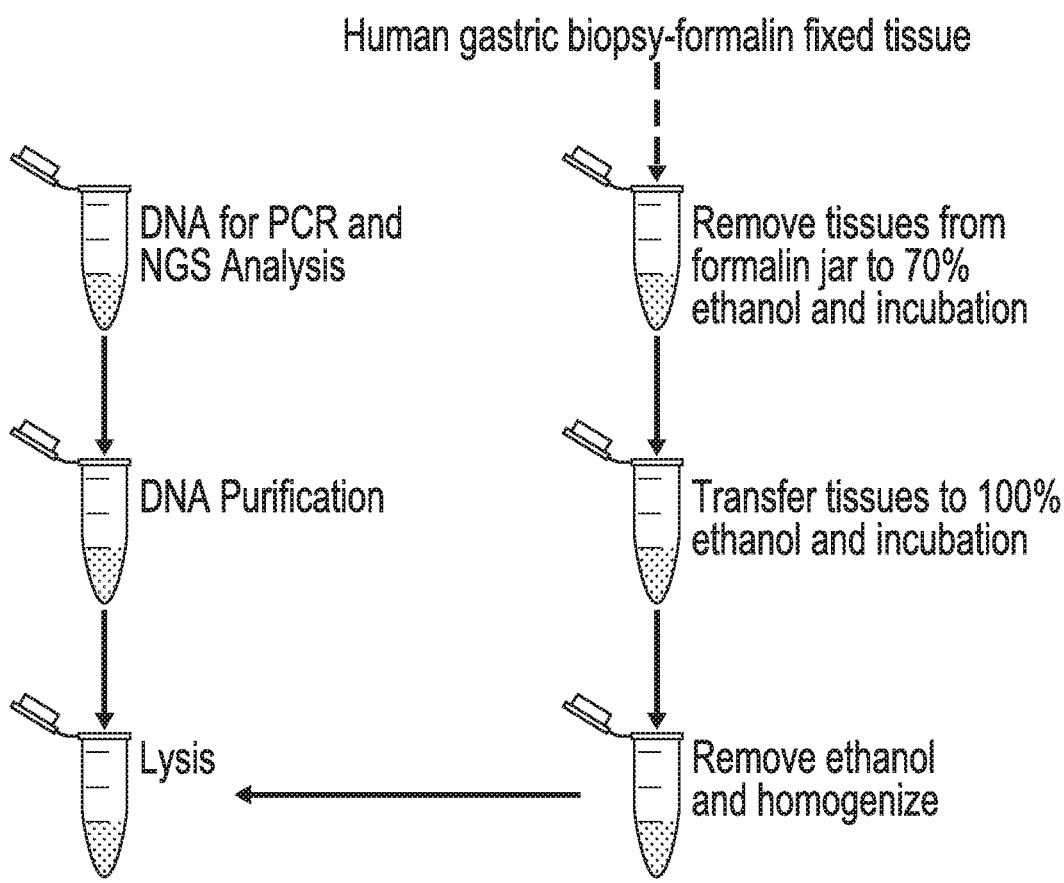
FIG. 2 is a flow chart depicting a method for obtaining *H. pylori* DNA from a biopsy that has been formalin fixed.

Also provided herein are methods for obtaining *H. pylori* DNA from a formalin-fixed sample. Such methods may comprise: processing a formalin-fixed sample to remove the formalin and extracting *H. pylori* DNA from the processed sample. FIG. 2 provides a flow chart depicting an exemplary method for obtaining *H. pylori* DNA from a human gastric biopsy formalin-fixed tissue sample.

Determining if Antibiotic Resistant *H. pylori* is Present in a Sample

Determining whether antibiotic *H. pylori* is present in a sample is critical to ensure proper, targeted treatment of *H. pylori* infections. The present disclosure provides methods for determining if antibiotic resistant *H. pylori* is present in a sample including, for example, determining if more than one strain of antibiotic resistant *H. pylori* are present in the sample. Such methods may comprise: obtaining a threshold level of *H. pylori* DNA from the sample (e.g., DNA from at least 10*H. pylori* genomes, at least 50 fragments of *H. pylori* DNA including, for example, between 50 and 100 fragments of *H. pylori* DNA), amplifying a region of the *H. pylori*

DNA to generate multiple copies of the region of the *H. pylori* DNA, sequencing the multiple copies of the region of the *H. pylori* DNA, comparing sequences of the multiple copies of the region of the *H. pylori* DNA to a reference sequence, identifying the presence of a mutation in the multiple copies of the region of the *H. pylori* DNA, and determining a number of the multiple copies of the region of the *H. pylori* DNA with the mutation, wherein antibiotic resistant *H. pylori* is present in the sample when the number of the multiple copies of the region of the *H. pylori* DNA with the mutation is above a predetermined amount (e.g., the region of the *H. pylori* DNA with the mutation is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98% or greater of the sequenced multiple copies of the region of the *H. pylori* DNA).

In some embodiments, the sample is a dental plaque, dental saliva, gastric juice, or a gastric biopsy. In other embodiments, the sample is formalin-fixed or formalin-fixed and paraffin embedded (FFPE). In some embodiments, the FFPE sample is a block. In other embodiments, the FFPE sample consists of sections of the sample or slides of the sample. In yet other embodiments, the sample is a fecal sample. In some embodiments, the sample is fresh. In other embodiments, the sample is frozen, in preservative, or in CLOtest Gel.

In embodiments where a fecal sample is used to determine if antibiotic resistant *H. pylori* is present in a sample, the fecal sample may be obtained by methods comprising: exposing a first part of the fecal sample to an anti-*H. pylori* antibody, separating *H. pylori* bound to the anti-*H. pylori* antibody from fecal material in the first part of the fecal sample, extracting *H. pylori* DNA from the *H. pylori* separated from the first fecal material, exposing a second part of the fecal sample to a DNA probe that binds to *H. pylori* DNA, extracting the *H. pylori* DNA from the second part of the fecal sample, and pooling the *H. pylori* DNA obtained from the first part of the fecal sample and the *H. pylori* DNA obtained from the second part of the fecal sample.

The inventors have surprisingly determined a threshold level (e.g., amount) of *H. pylori* DNA that is needed to determine if antibiotic resistant *H. pylori* is present in a sample.

TABLE 1

| Copy number | $C_T$ Value | Threshold $C_T$ for NGS Analysis |
|---|---|---|
| 100 | 29-30 | Any type of sample |
| 10 | 32-33 | Fresh biopsy, dental plaque, gastric juice |
| 2 | 35-36 | None of sample |

For example, Table 1 is a table listing the copy number and cycle threshold ($C_T$) of *H. pylori* DNA required from certain samples to enable use of the methods disclosed herein. The copy number is the number of copies of *H. pylori* genomes obtained from a sample. In real-time PCR, a positive reaction is detected by the accumulation of a fluorescent signal. The $C_T$ is the number of cycles required for the fluorescent signal to cross the threshold and exceed background level. The column Threshold $C_T$ for NGS Analysis indicates the type of sample, given the copy number and $C_T$, that can be used as the source for the *H. pylori* DNA. As shown in Table 1, any sample can be used if the copy number is 100 and the $C_T$ value is 29-30. However, no sample can be used, regardless of its source, if the copy number is 2 and the $C_T$ value is 35-36. If a sample's extracted *H. pylori* DNA meets the requirements in Table 1, it can be used in the disclosed method for determining if antibiotic resistant *H. pylori* is present in a sample.

A threshold level of *H. pylori* DNA may be obtained from the sample using the methods described herein, including methods to obtain *H. pylori* DNA from a fecal sample and methods to obtain *H. pylori* DNA from a formalin-fixed sample. Other known methods of obtaining DNA from a sample may be used provided such methods obtain a threshold level of *H. pylori* DNA. In an embodiment, a threshold level of *H. pylori* DNA is the DNA from at least 10 *H. pylori* genomes. In another embodiment, a threshold level of *H. pylori* DNA is the DNA from at least 50 fragments of *H. pylori* DNA. In yet another embodiment, a threshold level of *H. pylori* DNA is the DNA from between 50 and 100 fragments of *H. pylori* DNA.

Amplification of a region of the *H. pylori* DNA to generate multiple copies of the region of the *H. pylori* DNA can be carried out in a variety of ways. In an embodiment, segregational pooling of PCR primers and amplicons is used to amplify a region of the *H. pylori* DNA (see, e.g., PCT/US17/31901, incorporated herein by reference in its entirety). In another embodiment, nested or semi-nested PCR is used.

In one aspect the disclosure provides a set of PCR amplification primers to determine if antibiotic resistant *H. pylori* is present in a sample. Primers consisting of two pairs of primers (one forward and one reverse in each pair) for separate genes characteristic of known drug resistant *H. pylori* strains are listed in FIGS. 3A-3B. The example genes presented here include 16S rRNA (related to tetracycline resistance), 23S rRNA (related to clarithromycin resistance), pbp1 (related to resistance to penicillin antibiotics), gyrA (related to resistance to fluoroquinone antibiotics), rpoB (related to rifabutin resistance) and rdxA (involved in resistance to metronidazole), reference sequences of which are listed in FIGS. 3C-3D.

Those skilled in the art understand that other genetic loci involved in resistance to other antibiotics are known and may be included in or substituted for those described here. Practically, use of two primer pairs for each target gene (e.g., a region of the *H. pylori* DNA) minimizes the chance that any particular lesion (such as a cross-link or adduct) found in the target DNA sequences will inhibit PCR amplification from both amplicons, since such lesions are unlikely to occur at two different primer binding sites and involve all copies of the target gene within the target (template) DNA. However, the use of two pairs of primers targeting the same region of the bacterial chromosome, yet producing different but overlapping fragments requires that the PCR amplification reactions be carried out separately in order to avoid producing hybrid amplicons that do not match the full length amplicons each primer pair is designed to produce. Thus, at least two PCR amplification reactions must be performed for each set of primer pairs. In contrast, PCR primer pairs targeting different genes and producing amplicons with no homologous sequences can be pooled and thus the limited amount of target bacterial DNA that can be amplified from FFPE-preserved tissue used as efficiently as possible. The disclosure teaches segregation of primer pairs targeting an overlapping set of amplicons into separate pools and performing a single PCR amplification reaction on the segregated pools to produce the desired amplicons. In one example presented here, as many as 10 amplicons diagnostic for the five different types of drug resistant *H. pylori* genes listed above can be produced from just two PCR reactions using DNA extracted from FFPE gastric biopsy samples.

One embodiment of the disclosure is a method for detecting within a sample mutations in a plurality of genes (e.g., regions of *H. pylori* DNA), the method comprising a) identifying PCR primer pairs suitable for producing amplicons comprising regions of each of the genes containing one or more mutations, b) segregating PCR primer pairs comprising one or more primers that interfere with amplicon generation by another PCR primer pair into separate PCR primer pair pools, wherein each of the separate PCR primer pair pools contain a plurality of PCR primer pairs; c) generating amplicons from each of the separate PCR primer pair pools and target DNA isolated from the sample; d) combining all amplicons produced from each of the separate PCR primer pair pools and the target DNA into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different samples, and sequencing all indexed sample amplicons simultaneously; and e) identifying mutations within the indexed sequenced amplicons from a sample by reference to the wild-type sequence.

In another embodiment, the plurality of genes comprises genes (e.g., regions of *H. pylori* DNA) selected from the group consisting of *H. pylori* 16S rRNA, 23S rRNA, gyrA, rpoB, pbp1, and rdxA. In further embodiments, the identified mutation is an A2142G, A2143G, and/or A2142C mutation of the *H. pylori* 23S rRNA gene; an A928C, AG926-927GT, A926G/A928C and/or AGA926-928TTC mutation of the *H pylori* 16S rRNA gene; a C261A, C261G, G271A, and/or G271T mutation of the *H. pylori* gyrA gene encoding DNA gyrase subunit A; between codons 525 and 545 of the *H. pylori* rpoB gene encoding the beta/beta' subunit of DNA-directed RNA polymerase; a C1242A or C1242G mutation in the *H. pylori* pbp1 gene encoding penicillin-binding protein 1; or within the *H. pylori* rdxA gene. In another embodiment, the identified mutation produces a loss of function of *H. pylori* oxygen-insensitive (Type I) NAPD(P)H nitroreductase encoded by rdxA.

In one embodiment of the invention, the amplicons do not exceed 230 base pairs in length. In another embodiment, the amplicons are greater than 130 base pairs in length. In a further embodiment, the PCR primer pair comprising one or more primers that interfere with amplicon generation by another PCR primer pair interfere by forming cross pair primer-dimers or by forming cross pair truncated amplicons.

Another embodiment of the disclosure is directed to a method for detecting within a patient derived sample the presence of drug resistant *H. pylori*, the method comprising: a) generating amplicons from DNA (e.g., regions of *H. pylori* DNA) isolated from the patient derived sample and; i) PCR primer pair pool 1 comprising primers SEQ ID NOs. 1-10; ii) PCR primer pair pool 2 comprising primers SEQ ID Nos. 11-22; iii) PCR primer pair pool 3 comprising primers SEQ ID Nos. 23-28; iv) PCR primer pair pool 4 comprising primers SEQ ID Nos. 29-32; v) PCR primer pair pool 5 comprising primers SEQ ID Nos. 33-38; vi) PCR primer pair pool 6 comprising primers SEQ ID Nos. 39-44; b) combining all amplicons produced from PCR primer pair pools 1-6 in step a) into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different patient derived samples, and sequencing all indexed sample amplicons simultaneously; c) identifying mutations within the sequenced indexed sample amplicons by reference to SEQ ID Nos. 47-52, and d) determining the drug-resistant profile of *H. pylori* present in the patient-derived profile by the presence or absence of mutations identified in step c).

Yet another embodiment of the disclosure is directed to a method for detecting within a patient derived sample the presence of drug resistant *H. pylori*, the method comprising: a) generating amplicons from DNA (e.g., regions of *H. pylori* DNA) isolated from the patient derived sample and; i) PCR primer pair pool 1 comprising primers SEQ ID Nos. 23-28; ii) PCR primer pair pool 2 comprising primers SEQ ID Nos. 29-32; iii) PCR primer pair pool 3 comprising primers SEQ ID Nos. 33-38; iv) PCR primer pair pool 4 comprising primers SEQ ID Nos. 39-44; b) combining all amplicons produced from PCR primer pair pools 1-4 in step a) into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different patient derived samples, and sequencing all indexed sample amplicons simultaneously; c) identifying mutations within the sequenced indexed sample amplicons by reference to SEQ ID Nos. 47-52; and d) determining the drug-resistant profile of *H. pylori* present in the patient-derived profile by the presence or absence of mutations identified in step c).

In a further embodiment any of the amplicon pools described here can be sequenced by classical Sanger sequencing methods using one of the terminal primers to a single amplicon within the pool as a forward sequencing primer and the other terminal primer to that amplicon as a reverse sequencing primer. Alternatively, unique sequencing primers specific to each desired reaction for each individual amplicon within the amplicon pool can be used for the same purpose. In this way each of the amplicons can be directly sequenced from an amplicon pool. The amplicon pool may or may not be combined with other amplicon pools from the same FFPE extracted biopsy sample and the combined amplicons prepared for sequencing by addition of adaptors and indexing tags in preparation for Next Generation sequencing (NGS). Tagged amplicon pools derived from a single FFPE biopsy sample can be further combined with differentially tagged amplicon pools from different FFPE biopsy samples and the combined sample amplicon pools directly sequenced by high-throughput multiplex sequencing methods.

In some embodiments of each or any of the above or below mentioned embodiments, the amplicons do not exceed 230 base pairs in length. In another embodiment, the amplicons are greater than 130 base pairs in length. In a further embodiment, the PCR primer pair comprising one or more primers that interfere with amplicon generation by another PCR primer pair interfere by forming cross pair primer-dimers or by forming cross pair truncated amplicons.

In some embodiments, a process referred to as segregational pooling is used to amplify a region of the *H. pylori* DNA to generate multiple copies of the region of the *H. pylori* DNA. In an example, to verify the presence of *H. pylori* sequences within the total DNA samples from each biopsy sample, PCR amplification of a specific 125 base-pair fragment unique highly conserved region of the 23S rRNA gene of *H. pylori* was performed using PCR primers SEQ ID Nos: 45 and 46. The PCR product was purified and sequenced and confirmed to be specific to *H. pylori* by BLAST analysis [Altschul, S. F., Gish, W., Miller, W., Myers, E. W. & Lipman, D. J. (1990) "Basic local alignment search tool." J. Mol. Biol. 215:403-410]. The absence of the correct amplified product (amplicon) indicated no usable *H. pylori* DNA was present in the sample.

Samples that did produce the 125 base-pair *H. pylori* specific PCR amplicon were further investigated to determine the quality of the recovered DNA. To determine the suitability of the extracted DNA from FFPE gastric biopsy samples containing *H. pylori* for PCR amplification and sequencing, a multiplex PCR qualification assay was developed. This qualification assay involves PCR amplification of the human GAPDH gene encoding glyceraldehyde-3-phosphate dehydrogenase with a set of PCR primers capable of producing an amplicon ladder of 100, 200, 300, 400 and 500 base-pair fragments. FFPE DNA with no significant damage, with large fragment sizes and at relatively high concentration produces all five "rungs" of the amplicon ladder, whereas highly damaged and significantly fragmented DNA will not produce any of the expected amplicons. With our accumulated experience with this method, we rate DNA recovered from FFPE gastric biopsy samples as good if this test produces 2 to 5 bands of the amplicon ladder, intermediate if it produces only a single band, and poor if no bands are observed at all. The overall frequency of the number of amplicon bands observed across numerous FFPE extracted biopsy samples indicates that limiting analytical amplicon size to about 200 base-pairs or less provides the best balance between producing as much contiguous sequence as possible and avoiding PCR amplification terminating damage in the template DNA.

PCR amplification reactions using both freshly prepared or frozen *H. pylori* chromosomal DNA (as a positive control) and samples extracted from FFPE gastric biopsy samples (experimental samples) were performed with 1U of Taq DNA Polymerase, 10 mM dNTP mix in a 100 mM Tris-HCl, 500 mM KCl and 25 mM $MgCl_2$ buffer.

For samples analyzed by Sanger sequencing methods, the PCR primers in FIGS. 3A and 3B (SEQ ID NOs 1-44) were used as indicated with the thermal cycling parameters are: initial denaturing at 95° C. for 10 minutes, followed by 35 cycles of 30 seconds at 95° C., 30 seconds at 55° C. and 30 seconds at 72° C., then a final extension at 72° C. for 10 minutes. The resulting amplicons from each amplification reaction were purified with a MiniElute PCR Purification column following the manufacturer's instructions.

The purified amplicons were processed for Sanger sequencing with the 4337455) following the manufacturer's protocol. The PCR sequencing reaction was executed with the following thermal parameters: 95° C. for 1 minute, then 25 cycles of 95° C. for 30 seconds, 56° C. for 30 seconds and 60° C. for 1 minute. The primer extension reactions were processed with the Agencourt CleanSEQ kit (Beckman Coulter Life Sciences Cat. No. A29151) following the manufacturer's instructions. Samples were loaded and analyzed on an ABI 3500 Genetic Analyzer (Applied Biosystems). Raw sequence data was collected with 3500 Series Data Collection Software (Applied Biosystems) and assembled and aligned against reference sequences using Sequencher v 5.4 software (Gene Codes Corp.).

In the case of samples destined for NGS sequencing the Illumina overhang adapter sequence is added to the locus-specific primer sequences listed in FIGS. 3A-3B (SEQ ID NOs 1-44). The forward overhang sequence (added to the 5' side of the locus specific forward primer sequence) is TCGTCGGCAGCGTCAGATGTGTAT-AAGAGACAG (SEQ ID NO. 47) and the reverse overhang sequence (added to the 5' side of the locus specific reverse primer sequence) is GTCTCGTGGGCTCGGAG-ATGTGTATAAGA-GACAG (SEQ ID NO. 48). The first round PCR amplification thermal cycling parameters are: initial denaturing at 95° C. for 11 minutes, followed by 35 cycles of 30 seconds at 95° C., 1 minute at 59° C. and 1 minute at 72° C., then a final extension at 72° C. for 10 minutes. Second stage PCR reactions (involving addition of multiplex index adapters) involved thermal cycling parameters: 98° C. for 30 seconds, 17 cycles of 98° C. for 20 seconds, 60° C. for 30 seconds and 72° C. for 45 seconds and a final extension at 72° C. for 5 minutes. The libraries were then processed with the Agencourt AMPure XP kit (Beckman Coulter Life Sciences Cat. No. A63880) following the manufacturer's instructions, quantitated on a 2100 BioAnalyzer (Agilent Technologies) diluted as necessary and loaded onto the Illumina MiSeq sequencing instrument (Illumina, Inc.). Data analysis was performed using NextGENe V 2.4.1.1 software (SoftGenetics).

In one aspect of the invention, multiple loci encoding different forms of drug-resistance can be simultaneously characterized by segregating the PCR primers used to generate the diagnostic amplicons covering each of the targeted loci. PCR primer pairs comprising SEQ ID NOs: 1 and 2 for producing a 168 base-pair amplicon (16SrRNA 168) spanning positions 926-928 of the 16S rRNA gene of *H. pylori*. Virtually any mutation in these positions produces a low level of tetracycline resistance, while the triple mutation AGA926-928TTC is associated with very high levels of tetracycline resistance. A second primer pair comprising SEQ ID NOs: 11 and 12 produce a 162 base-pair amplicon (16SrRNA 162) also encompassing positions 926-928 of the *H. pylori* 16S rRNA. Another PCR primer pair comprising SEQ ID NOs: 3 and 4 produces a 194 base pair amplicon (23SrRNA 194) spanning positions 2142 and 2143 of the 23S rRNA gene of *H. pylori*. Mutation of these positions, particularly A2142G, A2142C and A2143G mutations are associated with clarithromycin resistance. A second primer pair comprising SEQ ID NOs: 13 and 14 produces a 170 base-pair amplicon (23SrRNA 170) which also spans positions 2142 and 2143 of the *H. pylori* 23S rRNA. Another PCR primer pair comprising SEQ ID NOs: 5 and 6 produces a 193 base-pair amplicon (gyrA 193) which spans the region encoding amino acid positions 87 to 91 of the A subunit of *H. pylori* gyrase, encoded by the gyrA gene. Mutations of Asn87 to Lys or Tyr and mutation of Asp91 to Gly, Asn or Tyr, individually or together are known to produce resistance to fluoroquinone antibiotics. A second PCR primer pair spanning this region of the *H. pylori* gyrA gene, comprising SEQ ID NOs: 15 and 16 produces a 139 base-pair amplicon (gyrA 139). A third PCR primer pair spanning the same region comprising SEQ ID NOs: 17 and 18 produce a 137 base-pair amplicon (gyrA 137). Another PCR primer pair comprising SEQ ID NOs: 7 and 8 produce a 159 base-pair amplicon (pbpA 159) which encompasses the sequence encoding amino acid position 414 of the *H. pylori* pbp1 gene. Mutation of the serine normally found at position 414 of penicillin-binding protein 1 to an arginine produces resistance to amoxicillin and other penicillin antibiotics. Another PCR primer pair, SEQ ID NOs: 19 and 20 produce a 140 base-pair amplicon (pbpA 140) that also encompasses the sequence encoding position 414 of *H. pylori* penicillin-binding protein 1. Another PCR primer pair comprising SEQ ID NOs: 9 and 10 produce a 228 base-pair amplicon encompassing codons 525 to 545 of the *H. pylori* rpoB gene encoding the 1343' subunit of RNA polymerase. Mutation of any of the codons within this region can confer resistance to rifabutin and other rifamycin-like antibiotics. A PCR primer pair comprising SEQ ID NOs: 21 and 22 also produces an amplicon (rpoB-R-167) which is 167 base-pairs and encompasses the critical codons within rpoB.

Each pair of PCR primers targeting a particular gene region potentially encoding a drug-resistant mutation are segregated into separate PCR primer pair pools containing one or more unique primer pairs targeting different genes. Thus, PCR amplification of each pool produces amplicons specific to the plurality of genes within each pool and minimizes the chance of PCR amplification artifacts such as primer-dimers or cross pair amplicon truncation caused by homologous pairing within overlapping amplicon sequences. As shown in FIG. 3B, pool 5GF comprises PCR primer pairs 16SrRNA 168, 23SrRNA 194, gyrA193, pbpA 159 and rpoB 228. When FFPE derived *H. pylori* target DNA is amplified with these primer pairs five unique amplicons of 159, 168, 193, 194 and 228 base-pairs are produced.

Amplicon pool 5GR (FIG. 3B) comprises PCR primer pairs 16SrRNA 162R, 23SrRNA 170R, gyrA 139R, gyrA 137R, pbpA 140 and rpoB-R-167. When FFPE derived *H. pylori* target DNA is amplified with these primer pairs as many as 8 amplicons are produced. Four of these are unique amplicons of 140, 162, 167 and 170 base-pairs (corresponding to the pbpA-specific amplicon, 16S rRNA-specific amplicon, the rpoB-specific amplicon and the 23S rRNA-specific amplicon, respectively). The remaining four amplicons represent permutations of the two pairs of gyrA-specific PCR primer pairs present in pool 5GR. These primer pairs partially overlap one another in the same direction such that four possible amplicons can be produced from the two pairs of primers. Because the partial overlap of primers is limited to primers that have the same strand orientation (direction) there is no risk of primer-dimer formation, and because the amplified sequence between the primers is identical (except for the absolute length of the amplified sequence) no cross-hybridization between amplicons will produce new sequences. Thus, the two pairs of semi-unique primers can be accommodated within the amplicon pool. In this case, these primers may produce as many as four homologous amplicons of 131, 137, 139 and 145 base-pairs. The sequence of these amplicons is identical from end to end with the sequence in each of the other amplicons—with the exception of the few base-pairs missing from the ends of the shorter amplicons, which are present in the longer amplicons.

Figure 4:
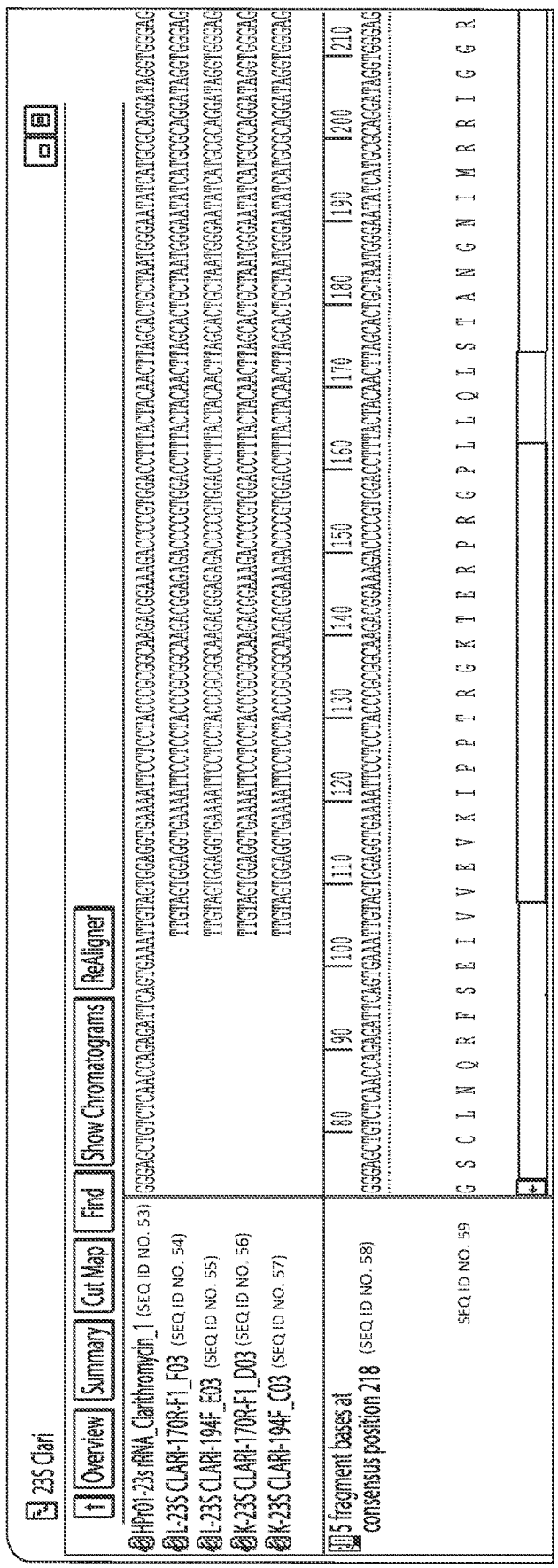
FIG. 4 depicts the *H. pylori* rdxA gene and illustrates the relative arrangement of the described amplicons.

Alignment of each of the sequenced amplicons allows identification of mutations conferring drug resistance. FIG. 4 (SEQ ID NOs 53-59) is an example of the A2142G mutation in the 23S rRNA identified in two independent FFPE derived sample ("E" and "K") that indicates that treatment of the *H. pylori* strains afflicting the patients from whom these samples were derived is unlikely to respond to clarithromycin. The top sequence is a known clarithromycin resistant strain of *H. pylori* while the two sequences immediately below the control are independent PCR amplicons from sample "E" and the last two sequences are independent amplicons from sample "F."

In another aspect of the invention, segregated PCR primer pools allow efficient coverage of an entire gene. Resistance to metronidazole can occur as a result of any loss of function mutation in the *H. pylori* rdxA gene encoding the bacterial oxygen-insensitive (Type I) NAD(P)H nitroreductase. Metronidazole is activated by the action of this enzyme and thus, any frameshift, or point mutation within the rdxA gene encoding this enzyme has the potential to confer resistance to metronidazole. Unlike the previously described embodiments, no single short amplicon can encompass the known mutational spectrum of metronidazole resistance encountered in *H. pylori*. To address this problem, two series of PCR primer pairs producing overlapping amplicons were designed such that the primers within each series produce short amplicons that together cover the entire coding region of the rdxA gene. The primers between the two series are located in unique positions, but some may be within the coding sequence of the rdxA gene offset by only a few bases in one direction relative to the analogous primers in the other series (in a manner similar to the partially overlapping gyrA primers within amplicon pool 5GR described in the previous paragraph). This strategy reduces the chance of a single cross-link or adduct present in the target DNA from entirely blocking production of an amplicon. The sequence derived from amplicons produced by one series of PCR primers can be assembled with amplicons produced from the other series of PCR primers to ensure that complete coverage of the rdxA gene is achieved from the total set of primer pools. Each series of primers is placed into one of two amplicon pools for each series so that amplicons within the series that may overlap and which are produced from primers that are prone to form primer-dimers are segregated into separate pools. In the case of the *H. pylori* rdxA gene, one series of five short amplicons collectively span the entire rdxA coding sequence. These five amplicons, from 5' to 3' comprise the rdxA 188 amplicon (produced from PCR primer pair SEQ ID NOs: 23 and 24), the rdxA-5-2-163 amplicon (produced from PCR primer pair SEQ ID NOs: 29 and 30), the rdxA 156 amplicon (produced from PCR primer pair SEQ ID NOs: 25 and 26), the rdxA 182 amplicon (produced from PCR primer pair SEQ ID NOs: 31 and 32) and the rdxA 177 amplicon (produced from PCR primer pair SEQ ID NOs: 27 and 28). Within this series PCR primer pairs producing amplicons rdxA 188, rdxA156 and rdxA 177 are placed into a single pool designated rdxA-F1, while PCR primer pairs producing amplicons rdxA-5-2-163 and rdxA 182 are combined into a different pool designated rdxA-F2 (FIG. 3A). In another series six short amplicons are used to span the entire *H. pylori* rdxA gene. These amplicons, arrayed 5' to 3' comprise the rdxA-R-150 amplicon (produced from PCR primer pair SEQ ID NOs: 33 and 34), the rdxA-R-187 amplicon (produced from PCR primer pair SEQ ID NOs: 39 and 40), the rdxA-R-164 amplicon (produced from PCR primer pair SEQ ID NOs: 35 and 36), the rdxA-R0174 amplicon (produced from PCR primer pair SEQ ID NOs: 41 and 42, the rdxA-R-171 amplicon (produced from PCR primer pair SEQ ID NOs: 37 and 38) and the rdxA-R-189 amplicon (produced from PCR primer pair SEQ ID NOs: 43 and 44). Within this series PCR primer pairs producing amplicons rdxA-R-150, rdxA-R-164 and rdxA-R-171 are combined into one pool designated rdxA-R1, while PCR primer pairs producing amplicons rdxA-R-187, rdxA-R-174 and rdxA-R-189 are combined into a different pool designated rdxA-R2 (FIG. 3A). These PCR primer pools are used to generate their cognate amplicons from *H. pylori* DNA extracted from FFPE biopsy samples. Depending on how the amplicons are to be sequenced amplicons from each PCR reaction may be further combined so that each series is represented by a single amplicon pool.

Figure 5:
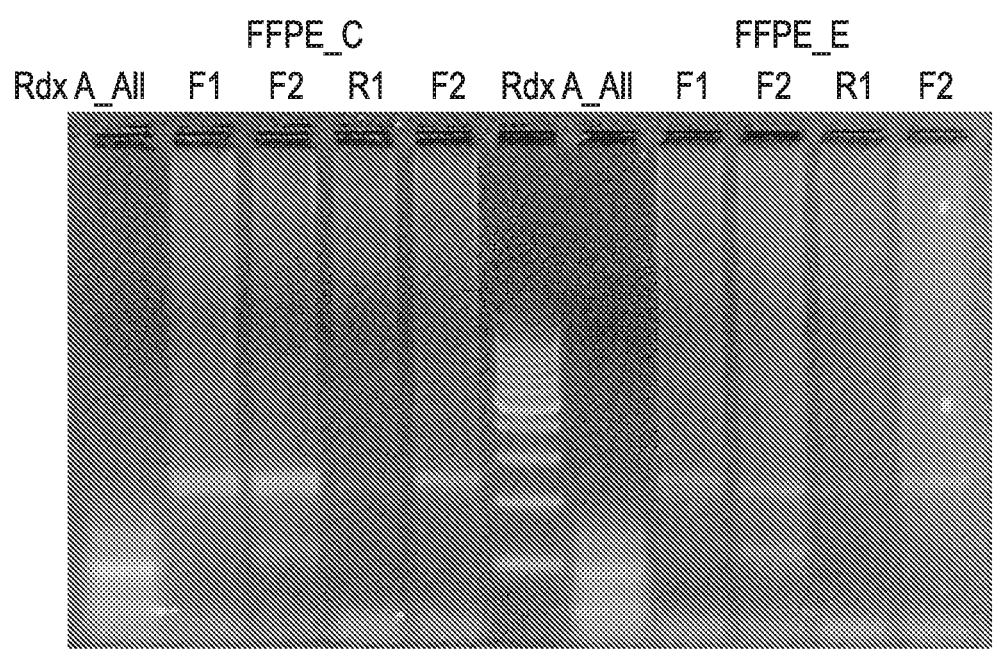
FIG. 5 is an electrophoresis gel demonstrating that pooling all rdxA specific primers generates incorrect sized amplicons, whereas the segregated primer pools described here generate correct sized amplicons.

As shown in FIG. 5 proper segregational pooling produces the correct (predicted) amplicons, whereas the same primers when present in a single pool produce a series of PCR products comprised of incorrect amplicons and primer dimers. Two FFPE samples. "FFPE C" and "FFPE E" were processed as described and served as target DNA for analysis of the rdxA gene. Lane 6 (counting from the left-most lane as lane 1) is a double-stranded DNA size marker (Ready-to-Use 100 bp DNA Ladder, Biotium, Inc.). The size marker is flanked on each side by sample specific pooled amplification products. Lanes 1 and 7 labeled "RDX-All" are the result of PCR amplification reactions containing all the PCR primers of the amplicons spanning the entire rdxA gene described above. The lanes marked "F1" (lanes 2 and 8) correspond to the rdxA-F1 pool comprising the rdxA 188, rdxA156 and rdxA 177 amplicon primes and both sample lanes contain amplicons between 150 and 200 base-pairs as predicted. The lanes marked "F2" (lanes 3 and 9) correspond to the rdxA-F2 pool comprising the rdxA-5-2-163 and rdxA 182 amplicon primers and both sample lanes contain amplicons of the correct size. Note that a minor product of about 60 base-pairs is also present, however this amplicon does not interfere in sequencing the correct amplicons and likely represents a product of internal recombination within or between one of the desired amplicons. The lanes marked "R1" (lanes 4 and 10) correspond to the rdxA-R1 pool comprising the rdxA-R-150, rdxA-R-164 and rdxA-R-171 amplicon primers and the desired amplicons are clustered on the gel between 150 and around 170 base-pairs. The lanes marked "R2" (lanes 5 and 11) correspond to the rdxA-R2 pool comprising the rdxA-R-187, rdxA-R-174 and rdxA-R-189 amplicon primers produce the proper sized amplicons.

FIG. 6 illustrates the ability of the method to determine the presence and pattern of drug and multi-drug resistance in multiple isolates derived from FFPE samples based on a single NGS analysis. In this case, the 5 separate genes analyzed as described in Example 1, as well as the rdxA gene analyzed as described in Example 2 are collated into a single report outlining the potential resistance profile of *H. pylori* in each patient-derived FFPE biopsy sample to each of the six drugs.

FIG. 7 also illustrates the ability of the method to determine the presence and pattern of drug and multi-drug resistance in multiple isolates derived from FFPE samples based on NGS analysis as described above. The table lists the genetic mutations found in each sample as well as the frequency of each mutation. The results show that NGS analysis can distinguish between FFPE samples that do not have any mutations versus those that do. For example, of the 24 samples, 10 (42%) had no mutations (Nos. 5, 6, 8, 9, 13, 17, and 21-24). However, the results also show that NGS analysis can detect both single and multiple mutations within one FFPE sample. For example, 14 samples (58%) had at least one gene mutation (Nos. 1-4, 7, 10-12, 14-16, and 18-20). Of these 14 samples, 11 samples had mutations in a single gene (Nos. 2, 4, 7, 11-12, 14-16, 18, 19, and 20) and 3 samples had mutations in multiple genes (Nos. 1, 3, and 10).

Of the samples with single gene mutations, 5 samples had gyrA gene mutations only (Nos. 2, 4, 15, 18, and 19), 2 samples had rdxA gene mutations only (Nos. 7 and 20), and 4 samples had 23S rRNA gene mutations only (Nos. 11, 12, 14, and 16). Of the samples with gyrA mutations only, one of the samples had two mutations with the gyrA gene (No. 19). As discussed above, the presence of gyrA gene mutations indicates fluoroquinone antibiotic resistance. Of the samples with rdxA gene mutations only, one of the samples had two mutations within the rdxA gene (No. 7). As discussed above, the presence of rdxA gene mutations indicates resistance to metronidazole.

The three samples with multiple gene mutations had mutations in both 23S rRNA and gyrA (Nos. 1 and 3) and both gyrA and rdxA (No. 10). The concurrent 23S rRNA and gyrA mutations indicate both clarithromycin and fluoroquinone antibiotic resistance; whereas, the concurrent gyrA and rdxA mutations indicate both fluoroquinone antibiotic resistance and metronidazole resistance.

Table 2 is a table of *H. pylori* genes and the antibiotic resistances associated with mutations in those genes.

TABLE 2

| *H. pylori* genes | Antibiotics Associated |
|---|---|
| 23S rRNA | Clarithromycin |
| gyrA | Fluoroquinolones |
| rdxA/frxA | Metronidazole |
| pbp1 | Amoxicillin |
| 16S rRNA | Tetracycline |
| rpoB | Rifabutin |

As a result, one or more of these genes can be used to as a basis to determine a region of the *H. pylori* DNA targeted for amplification. In an embodiment, the region of *H. pylori* DNA may be a *H. pylori* gene selected from the group comprising: 23S rRNA, gyrA, rdxA, frxA, pbp1, 16S rRNA, and rpoB. In another embodiment, the one or more mutations in the one or more amplified regions of *H. pylori* DNA are selected from the group comprising: A2143G and A2142G mutations in 23S rRNA; A272G Asp91Gly and G271A Asp91Asn in gyrA; pGlu194, G352A, pCys87, pR41Rfs in rdxA; and T926C and C927A in 16A rRNA.

The multiple copies of the region of the *H. pylori* DNA can be sequenced using methods, including, but not limited to high-throughput screening, pyrosequencing, sequencing-by-synthesis, single-molecule sequencing, nanopore sequencing, or semiconductor sequencing. Next generation sequencing or Sanger sequencing can be used to detect a mutation in the multiple copies of the region of the *H. pylori* DNA.

The steps of amplifying and sequencing the one or more regions of *H. pylori* DNA may comprise identifying PCR primer pairs suitable for producing amplicons comprising the one or more regions of the *H. pylori* DNA; segregating PCR primer pairs comprising one or more primers that interfere with amplicon generation by another PCR primer pair into separate PCR primer pair pools, wherein each of the separate PCR primer pair pools contain a plurality of PCR primer pairs; generating amplicons from each of the separate PCR primer pair pools and the *H. pylori* DNA; and combining all amplicons produced from each of the separate PCR primer pair pools and the *H. pylori* DNA into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different samples, and sequencing all indexed sample amplicons simultaneously. In an embodiment, mutations are identified within the indexed sequence amplicons from a sample by reference to corresponding wild type gene sequences.

In an embodiment, one or more reference sequences of the amplified regions of *H. pylori* DNA are provided. The sequences of the multiple copies of the region of the *H. pylori* DNA are compared to a reference sequence to identify the presence of a mutation. In a preferred embodiment, a library of *H. pylori* DNA sequences is prepared using next generation sequencing platforms, such as Illumina MiSeq or Thermo Fisher S5.

Comparison of the sequences of the multiple copies of the region of the *H. pylori* DNA to a reference sequence and identification of the presence of a mutation therein can be performed according to standard methods.

The sequences of the *H. pylori* DNA from the sample can be aligned with a reference sequence. Preferably, Burrows-Wheeler Aligner (BWA) is used to perform the sequence alignment. The sequence alignment can be used to identify the presence of a mutation in the multiple copies of the region of the *H. pylori* DNA. Additionally, a number of the multiple copies of the region of the *H. pylori* DNA with the mutation can be determined. In an embodiment, this number is a percentage indicating the frequency at which a mutation was detected in the *H. pylori* DNA from the sample.

Antibiotic resistant *H. pylori* is present in the sample when a number of the multiple copies of the region of the *H. pylori* DNA with the mutation is above a predetermined amount (e.g., the region of the *H. pylori* DNA with the mutation is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98% or greater of the sequenced multiple copies of the region of the *H. pylori* DNA). In a preferred embodiment, the predetermined amount is 5%; thus, the frequency at which a mutation is detected must be greater than 5% to indicate a real mutation conferring antibiotic resistance. Additionally, other criteria may be used to ensure the accuracy of the detection of a mutation. In an embodiment, the *H. pylori* DNA from the sample must have a minimum of 500 reads.

The antibiotic resistant *H. pylori* may be resistant to one or more of the following: macrolides, metronidazole, quinolones, rifamycins, amoxicillin, and tetracycline.

The methods disclosed herein may also be used to determine if multiple mutations in multiple strains of *H. pylori* are present in a sample. As discussed above, the methods may comprise obtaining a threshold level of *H. pylori* DNA from the sample, amplifying a region of the *H. pylori* DNA to generate multiple copies of the region of the *H. pylori* DNA, sequencing the multiple copies of the region of the *H. pylori* DNA, comparing sequences of the multiple copies of the region of the *H. pylori* DNA to a reference sequence, identifying the presence of a mutation in the multiple copies of the region of the *H. pylori* DNA, and determining a number of the multiple copies of the region of the *H. pylori* DNA with the mutation. In an embodiment, the region of the *H. pylori* DNA may comprise multiple *H. pylori* genes and may also contain multiple mutations of those genes. A number of the multiple copies of the region of the *H. pylori* DNA with the mutation may be determined for each *H. pylori* gene mutation that is amplified. If the number corresponding to a particular *H. pylori* gene mutation is 5% or greater, that indicates that mutation exists in the *H. pylori* DNA obtained from the sample. If the number is less than 5%, the *H. pylori* DNA obtained from the sample contains a wild-type version of the gene. If the number is 95% or greater, then there is likely one *H. pylori* strain in the sample with a mutation. However, if two or more *H. pylori* gene mutations are detected in a sample and the numbers for each gene are between 5% and 95%, then there are a mix of different *H. pylori* strains contained within the sample.

The present disclosure provides methods for treating *H. pylori* infection in a subject. The methods may comprise: obtaining a sample from the subject, obtaining a threshold level of *H. pylori* DNA from the sample, amplifying a region of the *H. pylori* DNA to generate multiple copies of the region of the *H. pylori* DNA, sequencing the multiple copies of the region of the *H. pylori* DNA, comparing sequences of the multiple copies of the region of the *H. pylori* DNA to one or more reference sequences, detecting a mutation in the multiple copies of the region of *H. pylori* DNA, determining a number of the multiple copies of the region of the *H. pylori* DNA with the mutation, wherein antibiotic resistant *H. pylori* is present in the sample when the number of the multiple copies of the region of the *H. pylori* DNA with the mutation is above a predetermined amount, and administering to the subject one or more antibiotics to which the *H. pylori* lacks resistance.

The threshold level of *H. pylori* DNA is DNA from at least 10 *H. pylori* genomes, at least 50 fragments of *H. pylori* DNA, between 50 and 100 fragments of *H. pylori* DNA)

The mutation may be determined to be above a predetermined amount where the region of the *H. pylori* DNA with the mutation is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98% or greater of the sequenced multiple copies of the region of the *H. pylori* DNA.

As used herein, the terms, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms.

The present disclosure is illustrated in the following Examples, which are set forth to aid in understanding the invention, but should not be construed to limit in any way the scope of the disclosure as defined in the claims that follow.

EXAMPLES

Example 1: Failure of a Traditional Therapy to Treat an *H. pylori* Infection

A 65-year-old male subject presented with a history of gastrointestinal complaints. He was treated for *H. pylori* infection with a standard 7-day treatment consisting of a proton pump inhibitor (PPI) at a dose of 20 mg b. d. (e.g., twice a day), clarithromycin at a dose of 500 mg b. d., and amoxicillin at a dose of 1 g b. d. The subject continued to experience persistent gastrointestinal disturbances. Because of this, the subject underwent an endoscopy and a biopsy sample was collected and analyzed using the disclosed methods and materials for determining if antibiotic resistant *H. pylori* is present. The results showed that the subject's *H. pylori* infection was resistant to clarithromycin and amoxicillin. As a result, alternative means of treating the infection were used.

Example 2: Multiple Treatment Failures

A 55-year-old female subject presented with a history of gastrointestinal complaints. She was treated for *H. pylori* infection with a standard 7-day treatment consisting of a proton pump inhibitor (PPI) at a dose of 20 mg b. d. (e.g., twice a day), clarithromycin at a dose of 500 mg b. d., and amoxicillin at a dose of 1 g b. d. Her symptoms persisted, so she was treated with a second line therapy. Her symptoms continued after this treatment. An *H. pylori* breath test was performed and showed that *H. pylori* was still present. Because of this, the subject underwent an endoscopy and a biopsy sample was collected and analyzed using the disclosed methods and materials for determining if antibiotic resistant *H. pylori* is present. The results showed that the subject's *H. pylori* infection was resistant to clarithromycin and amoxicillin. As a result, alternative means of treating the infection were used.

Example 3: Studies of *H. pylori* DNA Samples

A study was performed using *H. pylori* DNA samples that contained DNA for multiple different antibiotic resistant *H. pylori* strains. FIG. 8 is the report generated from various mixing experiments that were conducted using *H. pylori* DNA samples containing multiple antibiotic resistant *H. pylori* strains. The *H. pylori* genes analyzed were 23S rRNA, gyrA, rdxA, and 16S rRNA. Individual samples were analyzed to determine if antibiotic resistant *H. pylori* was present, including, sample ID numbers 1002, 1025, 1645, DG-1014, and DG-1008. As shown in FIG. 6, each of these samples contained mutations conferring antibiotic resistance, as indicated by a specific mutation and the number of the multiple copies of the region of the *H. pylori* DNA with a mutation, expressed as a percentage. For example, sample 1002 had *H. pylori* DNA that had an A214G mutation in 23S rRNA (the frequency of the mutation was over 5%), a A272G and Asp91Gly mutation in gyrA, and T926C, C927A, and T928G mutations in 16S rRNA. The sample's rdxA gene did not contain any mutations from the wild-type version of the gene. Sample 1025 had pGlu194 and G352A mutations in rdxA. When samples 1002 and 1025 were combined and analyzed using the disclosed techniques, all of the mutations detected in the individual samples were detected at numbers indicating that the mutations were real. This shows that the disclosed methods can be used to detect multiple mutations in multiple strains of *H. pylori* concurrently.

Figure 9:
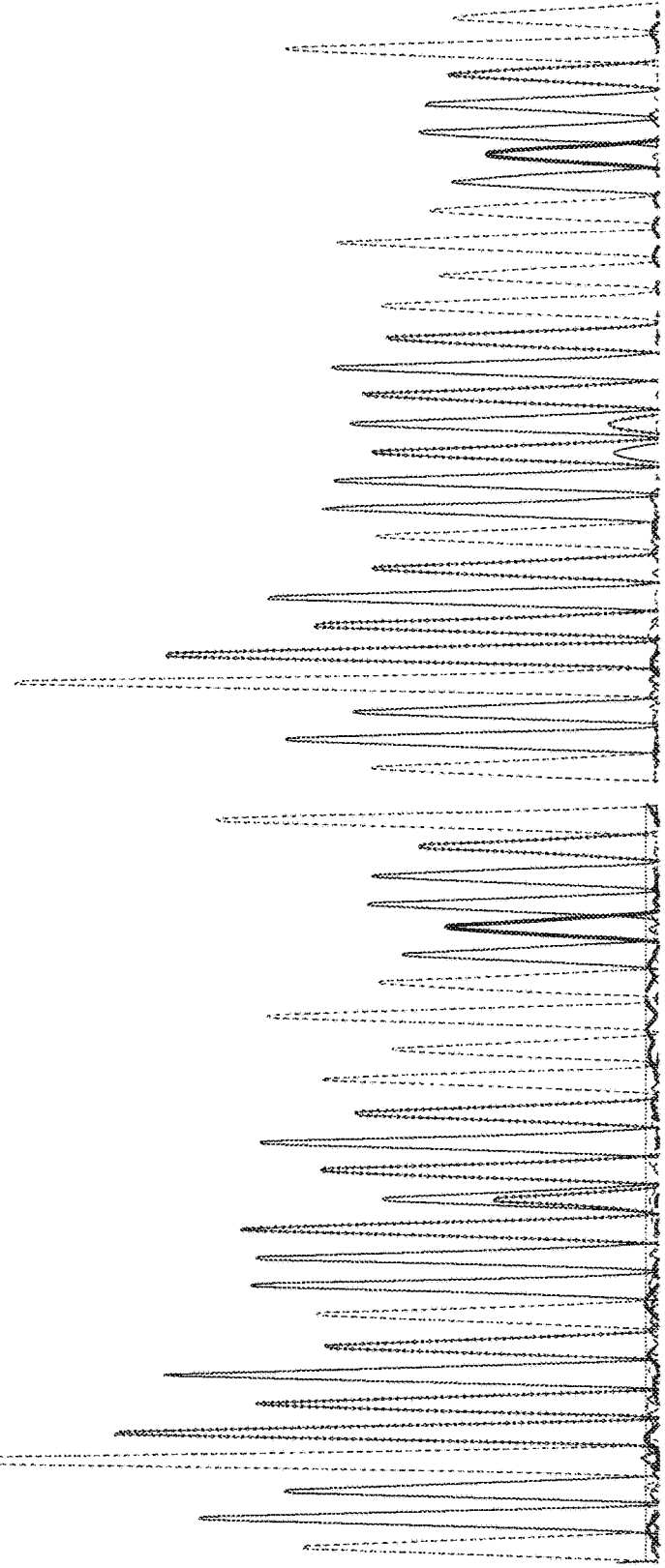
FIG. 9 is a graphical representation of Sanger sequencing of *H. pylori* DNA containing a mixture of different antibiotic resistant strains.

FIG. 9 is a graphic representation of the Sanger sequencing of *H. pylori* strains with mixed antibiotic resistance. As shown in FIG. 9, the number of the multiple copies of the region of the *H. pylori* DNA with a mutation was greater than 5%, indicating that the mutations exist in the *H. pylori* DNA from the depicted samples.

An *H. pylori* DNA sample was analyzed for the presence of a mutation in the 23S rRNA *H. pylori* gene and to determine whether the detection of that mutation indicated the presence of mixed *H. pylori* strains. FIG. 10A is a summary data table of the detection of a mutation in the 23S rRNA *H. pylori* gene that shows whether the detection of a mutation indicated mixed *H. pylori* strains. The data table lists the number of amplifications or "reads" of a sample from next generation sequencing, the number of the multiple copies of the region of the *H. pylori* DNA with a mutation, and whether the number of the multiple copies of the region of the *H. pylori* DNA with a mutation indicates the presence of antibiotic resistant *H. pylori*. As shown in FIG. 10A, if the number of the multiple copies of the region of the *H. pylori* DNA with a mutation of the 23S rRNA mutation is greater than 5%, but less than 95%, there are likely a mix of *H. pylori* strains present in the sample. If the number of the multiple copies of the region of the *H. pylori* DNA with a mutation is 5% or less, the 23S rRNA gene is the wild-type version of the gene (e.g., no mutations). However, if the number of the multiple copies of the region of the *H. pylori* DNA with a mutation of the mutation is 95% or greater, then there is likely one *H. pylori* strain in the sample that, in this case, is resistant to clarithromycin.

An *H. pylori* DNA sample was analyzed for the presence of a mutation in the 23S rRNA and gyrA *H. pylori* genes and to determine whether the detection of one or more mutations indicated the presence of mixed *H. pylori* strains. FIG. 10B is a summary data table of the detection of a mutation in the 23S rRNA and gyrA *H. pylori* genes that shows whether the detection of one or more mutations indicated mixed *H. pylori* strains. The data table lists the number of amplifications or "reads" of a sample from next generation sequencing, the number of the multiple copies of the region of the *H. pylori* DNA with a mutation, and whether the number of the multiple copies of the region of the *H. pylori* DNA with a mutation indicates the presence of antibiotic resistant *H. pylori*. FIG. 10B shows that if the number of the multiple copies of the region of the *H. pylori* DNA with a mutation of both mutations is 95% or greater, then there is one *H. pylori* strain in the sample that is resistant to both clarithromycin and fluoroquinolones. However, if the number of the multiple copies of the region of the *H. pylori* DNA with a mutation of both of the mutations are 5% or greater, but less than 95%, the sample contains a mix of *H. pylori* strains. If the number of the multiple copies of the region of the *H. pylori* DNA with a mutation of both mutations are less than 5% both genes are wild-type.

An *H. pylori* DNA sample was analyzed for the presence of a mutation in the 23S rRNA, gyrA, and rdxA *H. pylori* genes and to determine whether the detection of one or more mutations indicated the presence of mixed *H. pylori* strains. FIG. 10C is a summary data table of the detection of a mutation in the 23S rRNA, gyrA, and rdxA *H. pylori* genes that shows whether the detection of one or more mutations indicated mixed *H. pylori* strains. The data table lists the number of amplifications or "reads" of a sample from next generation sequencing, the number of the multiple copies of the region of the *H. pylori* DNA with a mutation, and whether the number of the multiple copies of the region of the *H. pylori* DNA with a mutation indicates the presence of antibiotic resistant *H. pylori*. FIG. 8C shows that if number of the multiple copies of the region of the *H. pylori* DNA with a mutation of all three mutations is 95% or greater, then there is one *H. pylori* strain in the sample that is resistant to clarithromycin, fluoroquinolones, and metronidaxole. However, if the number of the multiple copies of the region of the *H. pylori* DNA with a mutation of both of the mutations are 5% or greater, but less than 95%, the sample contains a mix of *H. pylori* strains. If the number of the multiple copies of the region of the *H. pylori* DNA with a mutation of both mutations are less than 5% both genes are wild-type.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary only, with the true scope and spirit of the disclosure being indicated by the following claims. All references, patents, and patent applications referred to in this application are herein incorporated by reference in their entirety.

What is claimed is:

1. A method for determining if antibiotic resistant *H. pylori* is present in a fecal sample, the method comprising:
   a) obtaining a threshold level of *H. pylori* DNA from the fecal sample, wherein the *H. pylori* DNA is obtained from the fecal sample by the method comprising:
      i) exposing a first part of the fecal sample to an anti-*H. pylori* antibody; ii) separating *H. pylori* bound to the anti-*H. pylori* antibody from fecal material in the first part of the fecal sample; iii) extracting *H. pylori* DNA from the *H. pylori* separated from the first fecal material; (iv) exposing a second part of the fecal sample to a DNA probe that binds to *H. pylori* DNA; (v) extracting the *H. pylori* DNA from the second part of the fecal sample; and (vi) pooling the *H. pylori* DNA obtained from the first part of the fecal sample and the *H. pylori* DNA obtained from the second part of the fecal sample;
   b) amplifying a region of the *H. pylori* DNA to generate multiple copies of the region of the *H. pylori* DNA;
   c) sequencing the multiple copies of the region of the *H. pylori* DNA;
   d) comparing sequences of the multiple copies of the region of the *H. pylori* DNA to a reference sequence;
   e) identifying the presence of a mutation in the multiple copies of the region of the *H. pylori* DNA; and
   f) determining a number of the multiple copies of the region of the *H. pylori* DNA with the mutation, wherein antibiotic resistant *H. pylori* is present in the fecal sample when the number of the multiple copies of the region of the *H. pylori* DNA with the mutation is above a predetermined amount.

2. The method of claim 1, wherein the mutation in the multiple copies of the region of the H. pylori DNA is detected by next generation sequencing.

3. The method of claim 1 further comprising the step of providing one or more reference sequences of the amplified regions of *H. pylori* DNA.

4. The method of claim 1, wherein the steps of amplifying and sequencing the one or more regions of *H. pylori* DNA comprise:
   a) identifying PCR primer pairs suitable for producing amplicons comprising the one or more regions of the *H. pylori* DNA;

b) segregating PCR primer pairs comprising one or more primers that interfere with amplicon generation by another PCR primer pair into separate PCR primer pair pools, wherein each of the separate PCR primer pair pools contain a plurality of PCR primer pairs;

c) generating amplicons from each of the separate PCR primer pair pools and the *H. pylori* DNA; and d) combining all amplicons produced from each of the separate PCR primer pair pools and the *H. pylori* DNA into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different samples, and sequencing all indexed sample amplicons simultaneously.

5. The method of claim 4, further comprising the step of identifying mutations within the indexed sequence amplicons from a sample by reference to corresponding wild type gene sequences.

6. The method of claim 1, wherein the region of *H. pylori* DNA is one or more *H. pylori* gene selected from the group comprising: 23S rRNA, gyrA, rdxA, frxA, pbp1, 16S rRNA, and rpoB.

7. The method of claim 1, wherein the threshold level of *H. pylori* DNA is DNA from at least 10 *H. pylori* genomes.

8. The method of claim 1, wherein the threshold level of *H. pylori* DNA is DNA from at least 50 fragments of *H. pylori* DNA.

9. The method of claim 1, wherein the threshold level of *H. pylori* DNA is DNA from between 50 and 100 fragments of *H. pylori* DNA.

10. The method of claim 1, wherein the antibiotic resistant *H. pylori* is resistant to one or more of the following: macrolides, metronidazole, quinolones, rifamycins, amoxicillin, and tetracycline.

11. A method for obtaining *H. pylori* DNA from a fecal sample, the method comprising:
    a) exposing a first part of the fecal sample to an anti-*H. pylori* antibody;
    b) separating *H. pylori* bound to the anti-*H. pylori* antibody from fecal material in the first part of the fecal sample;
    c) extracting *H. pylori* DNA from the *H. pylori* separated from the first fecal material;
    d) exposing a second part of the fecal sample to a DNA probe that binds to *H. pylori* DNA;
    e) extracting the *H. pylori* DNA from the second part of the fecal sample; and
    f) pooling the *H. pylori* DNA obtained from the first part of the fecal sample and the *H. pylori* DNA obtained from the second part of the fecal sample.

12. The method of claim 11, further comprising the step of homogenizing the fecal sample.

13. The method of claim 11, wherein the anti-*H. pylori* antibody is labeled.

14. The method of claim 13, wherein the anti-*H. pylori* antibody is labeled with biotin.

15. A method for treating *H. pylori* infection in a subject, the method comprising:
    a) obtaining a fecal sample from the subject;
    b) obtaining a threshold level of *H. pylori* DNA from the fecal sample;, wherein the *H. pylori* DNA is obtained from the fecal sample by the method comprising:
        i) exposing a first part of the fecal sample to an anti-*H. pylori* antibody; ii) separating *H. pylori* bound to the anti-*H. pylori* antibody from fecal material in the first part of the fecal sample; iii) extracting *H. pylori* DNA from the *H. pylori* separated from the first fecal material; (iv) exposing a second part of the fecal sample to a DNA probe that binds to *H. pylori* DNA; (v) extracting the *H. pylori* DNA from the second part of the fecal sample; and (vi) pooling the *H. pylori* DNA obtained from the first part of the fecal sample and the *H. pylori* DNA obtained from the second part of the fecal sample;
    c) amplifying a region of the *H. pylori* DNA to generate multiple copies of the region of the *H. pylori* DNA;
    d) sequencing the multiple copies of the region of the *H. pylori* DNA;
    e) comparing sequences of the multiple copies of the region of the *H. pylori* DNA to one or more reference sequences;
    f) detecting a mutation in the multiple copies of the region of *H. pylori* DNA;
    g) determining a number of the multiple copies of the region of the *H. pylori* DNA with the mutation, wherein antibiotic resistant *H. pylori* is present in the sample when the number of the multiple copies of the region of the *H. pylori* DNA with the mutation is above a predetermined amount; and
    h) administering to the subject one or more antibiotics to which the *H. pylori* lacks resistance.

* * * * *

SEQUENCE LISTING

```
<160> NUMBER OF SEQ ID NOS: 59

<210> SEQ ID NO 1
<211> LENGTH: 17
<212> TYPE: DNA
<213> ORGANISM: Artificial Sequence
<220> FEATURE:
<223> OTHER INFORMATION: PCR primer

<400> SEQUENCE: 1
taacgcatta agcatcc                                                    17

<210> SEQ ID NO 2
<211> LENGTH: 18
<212> TYPE: DNA
<213> ORGANISM: Artificial Sequence
<220> FEATURE:
<223> OTHER INFORMATION: PCR primer

<400> SEQUENCE: 2
```

```
ccagacactc cactattt                                                    18

<210> SEQ ID NO 3
<211> LENGTH: 15
<212> TYPE: DNA
<213> ORGANISM: Artificial Sequence
<220> FEATURE:
<223> OTHER INFORMATION: PCR primer

<400> SEQUENCE: 3
ccgacctgca tgaat                                                       15

<210> SEQ ID NO 4
<211> LENGTH: 15
<212> TYPE: DNA
<213> ORGANISM: Artificial Sequence
<220> FEATURE:
<223> OTHER INFORMATION: PCR primer

<400> SEQUENCE: 4
agccaaagcc cttac                                                       15

<210> SEQ ID NO 5
<211> LENGTH: 19
<212> TYPE: DNA
<213> ORGANISM: Artificial Sequence
<220> FEATURE:
<223> OTHER INFORMATION: PCR primer

<400> SEQUENCE: 5
tatgcgatgc atgaattag                                                   19

<210> SEQ ID NO 6
<211> LENGTH: 19
<212> TYPE: DNA
<213> ORGANISM: Artificial Sequence
<220> FEATURE:
<223> OTHER INFORMATION: PCR primer

<400> SEQUENCE: 6
catcaataga gccaaagtt                                                   19

<210> SEQ ID NO 7
<211> LENGTH: 17
<212> TYPE: DNA
<213> ORGANISM: Artificial Sequence
<220> FEATURE:
<223> OTHER INFORMATION: PCR primer

<400> SEQUENCE: 7
ttgataatgg ctattcc                                                     17

<210> SEQ ID NO 8
<211> LENGTH: 15
<212> TYPE: DNA
<213> ORGANISM: Artificial Sequence
<220> FEATURE:
<223> OTHER INFORMATION: PCR primer

<400> SEQUENCE: 8
ggctcaaggc ttctt                                                       15

<210> SEQ ID NO 9
<211> LENGTH: 20
<212> TYPE: DNA
<213> ORGANISM: Artificial Sequence
```

```
<220> FEATURE:
<223> OTHER INFORMATION: PCR primer

<400> SEQUENCE: 9
gacaagctca ctaccatgag                                             20

<210> SEQ ID NO 10
<211> LENGTH: 18
<212> TYPE: DNA
<213> ORGANISM: Artificial Sequence
<220> FEATURE:
<223> OTHER INFORMATION: PCR primer

<400> SEQUENCE: 10
cacatccctg gcttcaaa                                               18

<210> SEQ ID NO 11
<211> LENGTH: 17
<212> TYPE: DNA
<213> ORGANISM: Artificial Sequence
<220> FEATURE:
<223> OTHER INFORMATION: PCR primer

<400> SEQUENCE: 11
ctagcggatt ctctcaa                                                17

<210> SEQ ID NO 12
<211> LENGTH: 17
<212> TYPE: DNA
<213> ORGANISM: Artificial Sequence
<220> FEATURE:
<223> OTHER INFORMATION: PCR primer

<400> SEQUENCE: 12
cagtaatgca gctaacg                                                17

<210> SEQ ID NO 13
<211> LENGTH: 17
<212> TYPE: DNA
<213> ORGANISM: Artificial Sequence
<220> FEATURE:
<223> OTHER INFORMATION: PCR primer

<400> SEQUENCE: 13
catcaagggt ggtatct                                                17

<210> SEQ ID NO 14
<211> LENGTH: 17
<212> TYPE: DNA
<213> ORGANISM: Artificial Sequence
<220> FEATURE:
<223> OTHER INFORMATION: PCR primer

<400> SEQUENCE: 14
ttgtagtgga ggtgaaa                                                17

<210> SEQ ID NO 15
<211> LENGTH: 18
<212> TYPE: DNA
<213> ORGANISM: Artificial Sequence
<220> FEATURE:
<223> OTHER INFORMATION: PCR primer

<400> SEQUENCE: 15
cgttatcgcc atcaatag                                               18
```

```
<210> SEQ ID NO 16
<211> LENGTH: 19
<212> TYPE: DNA
<213> ORGANISM: Artificial Sequence
<220> FEATURE:
<223> OTHER INFORMATION: PCR primer

<400> SEQUENCE: 16
ggtgatgtga ttggtaaat                                              19

<210> SEQ ID NO 17
<211> LENGTH: 18
<212> TYPE: DNA
<213> ORGANISM: Artificial Sequence
<220> FEATURE:
<223> OTHER INFORMATION: PCR primer

<400> SEQUENCE: 17
ccatcaatag agccaaag                                               18

<210> SEQ ID NO 18
<211> LENGTH: 15
<212> TYPE: DNA
<213> ORGANISM: Artificial Sequence
<220> FEATURE:
<223> OTHER INFORMATION: PCR primer

<400> SEQUENCE: 18
atcgtgggtg atgtg                                                  15

<210> SEQ ID NO 19
<211> LENGTH: 17
<212> TYPE: DNA
<213> ORGANISM: Artificial Sequence
<220> FEATURE:
<223> OTHER INFORMATION: PCR primer

<400> SEQUENCE: 19
ttgataatgg ctattcc                                                17

<210> SEQ ID NO 20
<211> LENGTH: 16
<212> TYPE: DNA
<213> ORGANISM: Artificial Sequence
<220> FEATURE:
<223> OTHER INFORMATION: PCR primer

<400> SEQUENCE: 20
ggttacaagc cctaaa                                                 16

<210> SEQ ID NO 21
<211> LENGTH: 20
<212> TYPE: DNA
<213> ORGANISM: Artificial Sequence
<220> FEATURE:
<223> OTHER INFORMATION: PCR primer

<400> SEQUENCE: 21
tgggacaaat tcggccataa                                             20

<210> SEQ ID NO 22
<211> LENGTH: 17
<212> TYPE: DNA
<213> ORGANISM: Artificial Sequence
<220> FEATURE:
<223> OTHER INFORMATION: PCR primer
```

<400> SEQUENCE: 22
tttcatgggc ggtcagc                                              17

<210> SEQ ID NO 23
<211> LENGTH: 22
<212> TYPE: DNA
<213> ORGANISM: Artificial Sequence
<220> FEATURE:
<223> OTHER INFORMATION: PCR primer

<400> SEQUENCE: 23
tggtaattgt ttcgttaggg at                                        22

<210> SEQ ID NO 24
<211> LENGTH: 18
<212> TYPE: DNA
<213> ORGANISM: Artificial Sequence
<220> FEATURE:
<223> OTHER INFORMATION: PCR primer

<400> SEQUENCE: 24
tggcgatttc agcgattt                                             18

<210> SEQ ID NO 25
<211> LENGTH: 18
<212> TYPE: DNA
<213> ORGANISM: Artificial Sequence
<220> FEATURE:
<223> OTHER INFORMATION: PCR primer

<400> SEQUENCE: 25
aagcgcttca gcgttaat                                             18

<210> SEQ ID NO 26
<211> LENGTH: 18
<212> TYPE: DNA
<213> ORGANISM: Artificial Sequence
<220> FEATURE:
<223> OTHER INFORMATION: PCR primer

<400> SEQUENCE: 26
tgcatgctgt ggttgaat                                             18

<210> SEQ ID NO 27
<211> LENGTH: 24
<212> TYPE: DNA
<213> ORGANISM: Artificial Sequence
<220> FEATURE:
<223> OTHER INFORMATION: PCR primer

<400> SEQUENCE: 27
gaagagcgta tcaataagcc taaa                                      24

<210> SEQ ID NO 28
<211> LENGTH: 22
<212> TYPE: DNA
<213> ORGANISM: Artificial Sequence
<220> FEATURE:
<223> OTHER INFORMATION: PCR primer

<400> SEQUENCE: 28
atgccactcc ttgaactta at                                         22

<210> SEQ ID NO 29

```
<211> LENGTH: 23
<212> TYPE: DNA
<213> ORGANISM: Artificial Sequence
<220> FEATURE:
<223> OTHER INFORMATION: PCR primer

<400> SEQUENCE: 29
agcctccaat aatgcaacta tcc                                              23

<210> SEQ ID NO 30
<211> LENGTH: 22
<212> TYPE: DNA
<213> ORGANISM: Artificial Sequence
<220> FEATURE:
<223> OTHER INFORMATION: PCR primer

<400> SEQUENCE: 30
cataccacca ttaacgctga ag                                               22

<210> SEQ ID NO 31
<211> LENGTH: 18
<212> TYPE: DNA
<213> ORGANISM: Artificial Sequence
<220> FEATURE:
<223> OTHER INFORMATION: PCR primer

<400> SEQUENCE: 31
atgcttggcg tgagattc                                                    18

<210> SEQ ID NO 32
<211> LENGTH: 21
<212> TYPE: DNA
<213> ORGANISM: Artificial Sequence
<220> FEATURE:
<223> OTHER INFORMATION: PCR primer

<400> SEQUENCE: 32
ggcttattga tacgctcttc t                                                21

<210> SEQ ID NO 33
<211> LENGTH: 20
<212> TYPE: DNA
<213> ORGANISM: Artificial Sequence
<220> FEATURE:
<223> OTHER INFORMATION: PCR primer

<400> SEQUENCE: 33
atgccactcc ttgaacttta                                                  20

<210> SEQ ID NO 34
<211> LENGTH: 18
<212> TYPE: DNA
<213> ORGANISM: Artificial Sequence
<220> FEATURE:
<223> OTHER INFORMATION: PCR primer

<400> SEQUENCE: 34
gcatgcttga tcgctttg                                                    18

<210> SEQ ID NO 35
<211> LENGTH: 22
<212> TYPE: DNA
<213> ORGANISM: Artificial Sequence
<220> FEATURE:
<223> OTHER INFORMATION: PCR primer

<400> SEQUENCE: 35
```
atgcaactat ccaatcccat ta                                              22

<210> SEQ ID NO 36
<211> LENGTH: 24
<212> TYPE: DNA
<213> ORGANISM: Artificial Sequence
<220> FEATURE:
<223> OTHER INFORMATION: PCR primer

<400> SEQUENCE: 36
ccggagtctt ataaagttag agtg                                            24

<210> SEQ ID NO 37
<211> LENGTH: 18
<212> TYPE: DNA
<213> ORGANISM: Artificial Sequence
<220> FEATURE:
<223> OTHER INFORMATION: PCR primer

<400> SEQUENCE: 37
gtgcgctgca atttgttt                                                   18

<210> SEQ ID NO 38
<211> LENGTH: 19
<212> TYPE: DNA
<213> ORGANISM: Artificial Sequence
<220> FEATURE:
<223> OTHER INFORMATION: PCR primer

<400> SEQUENCE: 38
ttaaacgagc gccattctt                                                  19

<210> SEQ ID NO 39
<211> LENGTH: 21
<212> TYPE: DNA
<213> ORGANISM: Artificial Sequence
<220> FEATURE:
<223> OTHER INFORMATION: PCR primer

<400> SEQUENCE: 39
caaccaagta atcgcatcaa c                                               21

<210> SEQ ID NO 40
<211> LENGTH: 18
<212> TYPE: DNA
<213> ORGANISM: Artificial Sequence
<220> FEATURE:
<223> OTHER INFORMATION: PCR primer

<400> SEQUENCE: 40
catgggcgtg agcttaat                                                   18

<210> SEQ ID NO 41
<211> LENGTH: 25
<212> TYPE: DNA
<213> ORGANISM: Artificial Sequence
<220> FEATURE:
<223> OTHER INFORMATION: PCR primer

<400> SEQUENCE: 41
ctaactttat aagactccgg ataga                                           25

<210> SEQ ID NO 42
<211> LENGTH: 22
<212> TYPE: DNA

```
<213> ORGANISM: Artificial Sequence
<220> FEATURE:
<223> OTHER INFORMATION: PCR primer

<400> SEQUENCE: 42
tgtgatggtt actgataagg at                                              22

<210> SEQ ID NO 43
<211> LENGTH: 19
<212> TYPE: DNA
<213> ORGANISM: Artificial Sequence
<220> FEATURE:
<223> OTHER INFORMATION: PCR primers

<400> SEQUENCE: 43
ctggcgattt cagcgattt                                                  19

<210> SEQ ID NO 44
<211> LENGTH: 22
<212> TYPE: DNA
<213> ORGANISM: Artificial Sequence
<220> FEATURE:
<223> OTHER INFORMATION: PCR primer

<400> SEQUENCE: 44
tggtaattgt ttcgttaggg at                                              22

<210> SEQ ID NO 45
<211> LENGTH: 22
<212> TYPE: DNA
<213> ORGANISM: Artificial Sequence
<220> FEATURE:
<223> OTHER INFORMATION: PCR primer

<400> SEQUENCE: 45
acaacccaga ctaccaaata ag                                              22

<210> SEQ ID NO 46
<211> LENGTH: 19
<212> TYPE: DNA
<213> ORGANISM: Artificial Sequence
<220> FEATURE:
<223> OTHER INFORMATION: PCR primer

<400> SEQUENCE: 46
gtgagctgtt acgctttct                                                  19

<210> SEQ ID NO 47
<211> LENGTH: 500
<212> TYPE: DNA
<213> ORGANISM: Helicobacter pylori

<400> SEQUENCE: 47
gtaatccgta gagatcaaga ggaatactca ttgcgaggcg acctgctgga acattactga     60
cgctgattgc gcgaaagcgt ggggagcaaa caggattaga taccctggta gtccacgccc    120
taaacgatgg atgctagttg ttggagggct tagttttcca gtaatgcagc taacgcatta    180
agcatcccgc ctgggagta cggtcgcaag attaaaatca aggaataga cggggacccg      240 cacaagcggt ggagcatgtg gtttaattcg aagatacacg aagaaccttac ctaggcttg    300 acattgagag aatccgctag aaatagtgga gtgtctggct tgccagacct tgaaaacagg    360
tgctgcacgc tgtcgtcag ctcgtgtcgt gagatgttgg gttaagtccc gcaacgagcg     420 caacccctttt tcttagttgc taacaggtta tgctgagaac tctaaggata ctgcctccgt   480
```
aaggaggagg aaggtgggga                                                500

<210> SEQ ID NO 48
<211> LENGTH: 1500
<212> TYPE: DNA
<213> ORGANISM: Helicobacter pylori

<400> SEQUENCE: 48
caagtgataa taaaagggggg tagagccctg attgggctag gctgctcgc cgcggtacca      60 aaccctatca aacttcgaat acctttatc gtatcttggg agtcaggcgg tgggtgataa     120
aatcaatcgt caaagggga acaacccaga ctaccaaata aggtccctaa gttctattct     180
gagtggaaaa agatgtgtgg ctactcaaac aaccaggagg ttggcttaga agcagccatc     240
ctttaaagaa agcgtaacag ctcactggtc tagtggtcat gcgctgaaaa tataacgggg     300
ctaagataga caccgaattt gtagattgtg ttaaacacag tggtagaaga gcgttcatac     360
cagcgttgaa ggtataccgg taaggagtgc tggagcggta tgaagtgagc atgcaggaat     420
gagtaacgat aagatatatg agaattgtat ccgccgtaaa tctaaggttt cctacgcgat     480
ggtcgtcatc gtagggttag tcgggtccta agccgagtcc gaaagggta ggtgatggca     540 aattggttaa tattccaata ccgactgtgg agcgtgatgg ggggacgcat agggttaagc     600
gagctagctg atggaagcgc tagtctaagg gcgtagattg gagggaaggc aaatccacct     660
ctgtatttga aacccaaaca ggctcttga gtccttttag acaaaggga gaatcgctga     720 taccgtcgtg ccaagaaaag tctctaagca tatccatagt cgtccgtacc gcaaaccgac     780
acaggtagat gagatgagta ttctaaggcg cgtgaaagaa ctctggttaa ggaactctgc     840
aaactagcac cgtaagttcg cgataaggtg tgccacagcg atgtggtctc agcaaagagt     900
ccctcccgac tgtttaccaa aaacacagca ctttgccaac tcgtaagagg aagtataagg     960
tgtgacgcct gcccggtgct cgaaggttaa gaggatgcgt cagtcgcaag atgaagcgtt    1020
gaattgaagc ccgagtaaac ggcggccgta actataacgg tcctaaggta gcgaaattcc    1080
ttgtcggtta ataccgacc tgcatgaatg gcgtaacgag atgggagctg tctcaaccag    1140
agattcagtg aaattgtagt ggaggtgaaa attcctccta ccccgcggca aacggaaaga    1200
ccccgtggac ctttactaca acttagcact gctaatggga atatcatgcg caggataggt    1260
gggaggcttt gaagtaaggg cttggctct tatggagcca tccttgagat accacccttg    1320
atgtttctgt tagctaactg gcctgtgtta tccacaggca ggacaatgct tggtgggtag    1380
tttgactggg gcggtcgcct cctaaaaagt aacggaggct tgcaaaggtt ggctcattgc    1440
ggttggaaat cgcaagttga gtgtaatggc acaagccagc ctgactgtaa gacatacaag    1500

<210> SEQ ID NO 49
<211> LENGTH: 550
<212> TYPE: DNA
<213> ORGANISM: Helicobacter pylori

<400> SEQUENCE: 49
atgcaagata attcagtcaa tgaaacaaaa aatattgtag aagtgggggat tgattcttct      60 attgaagaga gctatttagc ttattccatg agcgtgatca tagggcgcgc tttaccggac     120
gctagagatg gcttaaagcc cgtgcatagg cgtatttttgt atgcgatgca tgaattaggc     180
cttacttcaa aagtcgctta caaaaaaagc gctaggatcg tgggtgatgt gattggtaaa     240
taccaccccc atggcgataa tgcggtttat gatgcgctag tgagaatggc gcaagatttt     300

```
tccatgcgtt tggaattagt ggatgggcag ggcaactttg gctctattga tggcgataac    360
gccgcagcga tgcgttacac tgaagccaga atgactaagg cgagtgaaga aattttaagg    420
gatattgata agacaccat tgattttgtg cctaattatg acgataccttt aaaagagcca    480 gatattttac caagccgtct gcctaacctt ttagtcaatg gggctaatgg gatcgctgtg    540
gggatggcga                                                          550
```

<210> SEQ ID NO 50
<211> LENGTH: 500
<212> TYPE: DNA
<213> ORGANISM: Helicobacter pylori

<400> SEQUENCE: 50

```
aactaacgcg tctaatgaag atgaagacaa cttaaacgct agcatgatcg ttacagacac    60
gagcaccggt aagattttag ctttagtggg ggggattgat tataaaaaaa gcgctttcaa    120
tcgcgccacg caagccaaac ggcagtttgg gagcgcgata aagccttttg tgtatcagat    180
cgcttttgat aatggctatt ccacgacttc taaaatccct gataccgcgc gaaactttga    240
aaatggcaat tatagtaaaa acagtgaaca aaaccacgca tggcaccccca gcaattattc    300 tcgcaagttt ttagggcttg taaccttgca agaagccttg agccattcgt taaatctagc    360
cacgatcaat ttaagcgatc agcttggctt tgaaaaaatt tatcaatctt aagcgatat    420 ggggtttaaa aacctcccta aggacttgtc tattgtgtta gggagctttg ctatctcacc    480
cattgatgca gctgaaaagt                                                500
```

<210> SEQ ID NO 51
<211> LENGTH: 600
<212> TYPE: DNA
<213> ORGANISM: Helicobacter pylori

<400> SEQUENCE: 51

```
atgaagatat tatcaccacc gttaaatacc tcatgaagat caaaaacaat caaggcaaga    60
ttgatgacag ggaccacttg gcaatcgta ggattagggc ggtaggggaa ttgttggcca    120
atgaattgca ttcaggttta gtgaaaatgc aaaagaccat taaagacaag ctcactacca    180
tgagcggggc ttttgattcg ctcatgcccc atgacttggt caattctaaa atgatcacaa    240
gcaccatcat ggaatttttc atgggcggtc agctctcgca attttatggat caaacgaatc    300 ccttgagtga ggttacgcac aagcgccgcc tttcagcgct cggcgaaggg gggttggtga    360
aagacagagt ggggtttgaa gccagggatg tgcaccccac gcattatggc cgaatttgtc    420
ccattgagac cccagaaggt caaaatatcg gtctgatcaa cacccttttcc actttcacaa    480 gagtgaatga tttaggcttt attgaagccc cttataaaaa ggttgtggat ggcaaggtcg    540
tgggtgagac gatttatttg accgctattc aagaagacag ccacatcatc gctcccgcaa    600
```

<210> SEQ ID NO 52
<211> LENGTH: 1032
<212> TYPE: DNA
<213> ORGANISM: Helicobacter pylori

<400> SEQUENCE: 52

```
atttgagcat ggggcagatt ttaagcttat ttatggtaat tgtttcgtta gggattttat    60
tgtatgctac aaaaaattct aaaaaaataa aggaaaatca atgaaatttt tggatcaaga    120
aaaaagaaga caattattaa acgagcgcca ttccttgcaag atgttgata gccattatga    180 gttttctagc acagaattag aagaaatcgc tgaaatcgcc aggctatcgc caagctctta    240
```

-continued

```
caacacgcag ccatggcatt ttgtgatggt tactgataag gatttaaaaa aacaaattgc    300
agcgcacagc tatttcaatg aagagatgat taaaagcgct tcagcgttaa tggtggtatg    360
ctctttaaga cccagcgagt tgttaccaca cggccactac atgcaaaatc tctatccgga    420
gtcttataaa gttagagtga tcccctcttt tgctcaaatg cttggcgtga gattcaacca    480
cagcatgcaa agattagaaa gctatatttt agagcaatgc tatatcgctg tggggcaaat    540
ttgcatgggc gtgagcttaa tgggattgga tagttgcatt attggaggct ttgatccttt    600
aaaggtgggc gaagttttag aagagcgtat caataagcct aaaatcgcat gcttgatcgc    660
tttgggcaaa gggtggcaga agcgagtcaa aaatcaagaa atcaaaagt tgatgcgatt     720 acttggttgt gattaaacaa aatcaaaaac ttttttaacta taatcaaacc taaattaaag   780
ttcaaggagt ggcattttgt ttaaaagaat ggttttaatc gctcttttag gggtgttttc    840
aagcgtttca ttaagcgcta agagtctttt aagagatgat gggattttag tctctgattt    900
aaagggcatg aaatcagaac tatctgatgc tcctgcttgg gtttttgaag acgctaaagc    960
cccctacgaa gaaatgggcg tggcgtatat ccctgttaat aataaatatt tagggattga    1020
gcaagcgacc tt                                                        1032

<210> SEQ ID NO 53
<211> LENGTH: 143
<212> TYPE: DNA
<213> ORGANISM: Helicobacter pylori

<400> SEQUENCE: 53
gggagctgtc tcaaccagag attcagtgaa attgtagtgg aggtgaaaat tcctcctacc    60
cgcggcaaga cggaaagacc ccgtggacct ttactacaac ttagcactgc taatgggaat   120
atcatgcgca ggataggtgg gag                                          143

<210> SEQ ID NO 54
<211> LENGTH: 112
<212> TYPE: DNA
<213> ORGANISM: Artificial Sequence
<220> FEATURE:
<223> OTHER INFORMATION: Amplicon

<400> SEQUENCE: 54
ttgtagtgga ggtgaaaatt cctcctaccc gcggcaagac ggagagaccc cgtggacctt    60
tactacaact tagcactgct aatgggaata tcatgcgcag gataggtggg ag           112

<210> SEQ ID NO 55
<211> LENGTH: 112
<212> TYPE: DNA
<213> ORGANISM: Artificial Sequence
<220> FEATURE:
<223> OTHER INFORMATION: Amplicon

<400> SEQUENCE: 55
ttgtagtgga ggtgaaaatt cctcctaccc gcggcaagac ggagagaccc cgtggacctt    60
tactacaact tagcactgct aatgggaata tcatgcgcag gataggtggg ag           112

<210> SEQ ID NO 56
<211> LENGTH: 112
<212> TYPE: DNA
<213> ORGANISM: Artificial Sequence
<220> FEATURE:
<223> OTHER INFORMATION: Amplicon
```

```
<400> SEQUENCE: 56
ttgtagtgga ggtgaaaatt cctcctaccc gcggcaagac ggaaagaccc cgtggaccett    60 tactacaact tagcactgct aatgggaata tcatgcgcag gataggtggg ag            112

<210> SEQ ID NO 57
<211> LENGTH: 112
<212> TYPE: DNA
<213> ORGANISM: Artificial Sequence
<220> FEATURE:
<223> OTHER INFORMATION: Amplicon

<400> SEQUENCE: 57
ttgtagtgga ggtgaaaatt cctcctaccc gcggcaagac ggaaagaccc cgtggaccett    60 tactacaact tagcactgct aatgggaata tcatgcgcag gataggtggg ag            112

<210> SEQ ID NO 58
<211> LENGTH: 143
<212> TYPE: DNA
<213> ORGANISM: Helicobacter pylori

<400> SEQUENCE: 58
gggagctgtc tcaaccagag attcagtgaa attgtagtgg aggtgaaaat tcctcctacc    60
cgcggcaaga cggaaagacc ccgtggacct ttactacaac ttagcactgc taatgggaat   120
atcatgcgca ggataggtgg gag                                           143

<210> SEQ ID NO 59
<211> LENGTH: 48
<212> TYPE: PRT
<213> ORGANISM: Helicobacter pylori

<400> SEQUENCE: 59

Gly Ser Cys Leu Asn Gln Arg Phe Ser Glu Ile Val Val Glu Val Lys
1               5                   10                  15

Ile Pro Pro Thr Arg Gly Lys Thr Glu Arg Pro Arg Gly Pro Leu Leu
            20                  25                  30

Gln Leu Ser Thr Ala Asn Gly Asn Ile Met Arg Arg Ile Gly Gly Arg
        35                  40                  45
```